(12) United States Patent
Schneider et al.

(10) Patent No.: US 9,808,651 B2
(45) Date of Patent: Nov. 7, 2017

(54) TREATMENT OF ANXIETY DISORDERS BY EXTERNAL APPLICATION OF IONIZING RADIATION

(71) Applicants: M. Bret Schneider, Portola Valley, CA (US); John R. Adler, Jr., Stanford, CA (US)

(72) Inventors: M. Bret Schneider, Portola Valley, CA (US); John R. Adler, Jr., Stanford, CA (US)

(\*) Notice: Subject to any disclaimer, the term of this patent is extended or adjusted under 35 U.S.C. 154(b) by 983 days.

(21) Appl. No.: 13/900,131

(22) Filed: May 22, 2013

(65) Prior Publication Data

US 2014/0155677 A1 Jun. 5, 2014

Related U.S. Application Data

(60) Provisional application No. 61/651,470, filed on May 24, 2012.

(51) Int. Cl.
*A61N 5/10* (2006.01)
*A61N 5/06* (2006.01)

(52) U.S. Cl.
CPC ......... *A61N 5/1031* (2013.01); *A61N 5/1039* (2013.01); *A61N 5/1049* (2013.01);
(Continued)

(58) Field of Classification Search
CPC .. A61N 5/1031; A61N 5/1038; A61N 5/1039; A61N 5/1042; A61N 5/1045;
(Continued)

(56) References Cited

U.S. PATENT DOCUMENTS 2,638,554 A 5/1953 Bartow et al.
5,748,700 A 5/1998 Shepherd et al.
(Continued)

FOREIGN PATENT DOCUMENTS

WO WO 2013/176991 A1 11/2013

OTHER PUBLICATIONS

Hyman et al., "Addiction and the Brain: The Neurobiology of Compulsion and Its Persistence", Nature Reviews: Neuroscience 2001; 2: 695-703.
(Continued)

*Primary Examiner* — Charles A Marmor, II
*Assistant Examiner* — Carrie R Dorna
(74) *Attorney, Agent, or Firm* — Kilpatrick, Townsend & Stockton, LLP

(57) ABSTRACT

Medical systems, devices, and methods provide improved radiosurgical techniques for treatment of anxiety disorders (such as Post-Traumatic Stress Disorder (PTSD), Generalized Anxiety Disorder (GAD), Panic Disorder, Social Phobia, Specific Phobia, and the like). Radiation can be directed from a radiation source outside the patient toward a target tissue deep within the patient's brain using a stereotactic radiosurgical platform, typically without having to impose the surgical trauma associated with accessing deep brain tissues. The target will often include at least a portion of the amygdala, with exemplary treatments being directed to targets that are limited to a sub-region of the amygdala. Rather than applying sufficient radiation to kill the neural tissue within the target, a cellularly sub-lethal dose of the radiation may be applied. Without imposing frank cell death throughout the target, the radiation can mitigate the anxiety disorder, obesity, or the like, often by modulating the level of neural activity within the target and in associated tissues.

18 Claims, 16 Drawing Sheets

(52) U.S. Cl.
CPC .......... *A61N 5/1084* (2013.01); *A61N 5/0618* (2013.01); *A61N 5/1042* (2013.01)

(58) Field of Classification Search
CPC .. A61N 5/1049; A61N 5/1065; A61N 5/1069; A61N 5/107; A61N 5/1077; A61N 5/1081–5/1084; A61N 1/36082; A61N 1/36096
See application file for complete search history.

(56) References Cited

U.S. PATENT DOCUMENTS

| | | | |
|---|---|---|---|
| 5,997,176 | A | 12/1999 | Fairleigh |
| 6,501,981 | B1 | 12/2002 | Schweikard et al. |
| 7,085,347 | B2 | 8/2006 | Mihara et al. |
| 7,860,552 | B2 | 12/2010 | Borsook et al. |
| 8,337,382 | B2 | 12/2012 | Schneider et al. |
| 8,747,292 | B2 | 6/2014 | Schneider et al. |
| 2002/0074559 | A1 | 6/2002 | Dowling et al. |
| 2006/0257316 | A1 | 11/2006 | Madras et al. |
| 2009/0088680 | A1 | 4/2009 | Aravanis et al. |
| 2009/0114849 | A1* | 5/2009 | Schneider ............... A61N 5/10 250/492.1 |
| 2010/0057160 | A1* | 3/2010 | De Ridder ............ A61N 1/3605 607/45 |
| 2011/0082326 | A1 | 4/2011 | Mishelevich et al. |
| 2011/0098779 | A1 | 4/2011 | Schneider et al. |
| 2011/0130615 | A1 | 6/2011 | Mishelevich et al. |
| 2011/0213200 | A1 | 9/2011 | Mishelevich et al. |
| 2012/0290058 | A1* | 11/2012 | Langevin ............... A61M 21/02 607/116 |
| 2014/0235920 | A1 | 8/2014 | Schneider et al. |

OTHER PUBLICATIONS

Kandel et al., "Principles of Neural Science 4th Edition", New York: McGraw-Hill Companies Inc, 2000. 1002-1006.

Lewine et al., "Differences in Qualitative Brain Morphology Findings in Schizophrenia, Major Depression, Bipolar Disorder, and Normal Volunteers", Schizophrenia Research 1995; 15: 253-259.

Maltby et al., "Dysfunctional Action Monitoring Hyperactivates Frontal-striatal Circuits in Obsessive-Compulsive Disorder: an Event-related fMRI study", Neuroimage 2005; 24:495-503.

Pellmar et al., "Time-and Dose-Dependent Changes in Neuronal Activity Produced by X Radiation in Brain Slices", Radiation Research 1990; 122: 209-214.

Pizzagali et al., "Anterior Cingulate Activity as a Predictor of Degree of Treatment Response in Major Depression: Evidence from Brain Electrical Tomography Analysis", American Journal of Psychiatry 2001; 158: 405-415.

Tracy et al., "The Hippocampus and Motivation Revisited: Appetite and Activity", Behavioral Brain Research 2001; 127: 13-23.

Regis et al., "Gamma Knife Surgery, a Neuromodulation Therapy in Epilepsy Surgery!", Acta Neorochirurgica Supplements, vol. 84, 2002, pp. 37-47.

Notification of Transmittal of the International Search Report and the Written Opinion of the International Searching Authority, or the Declaration; International Search Report and Written Opinion of the International Searching Authority for corresponding International Application No. PCT/US2013/041626 dated Oct. 21, 2013, 10 pages.

Non-Final Office Action for U.S. Appl. No. 12/261,347 dated Dec. 22, 2011, 22 pages.

Final Office Action for U.S. Appl. No. 12/261,347 dated Jun. 21, 2012, 17 pages.

Notice of Allowance for U.S. Appl. No. 12/261,347 dated Oct. 12, 2012, 7 pages.

Non-Final Office Action for U.S. Appl. No. 13/708,076 dated Sep. 10, 2013, 16 pages.

Notice of Allowance for U.S. Appl. No. 13/708,076 dated Jan. 30, 2014, 11 pages.

Non-Final Office Action for U.S. Appl. No. 14/266,090 dated Aug. 13, 2014, 11 pages.

\* cited by examiner

TREATMENT OF ANXIETY DISORDERS BY EXTERNAL APPLICATION OF IONIZING RADIATION

CROSS-REFERENCES TO RELATED APPLICATIONS

The present application claims the benefit of U.S. Provisional Appln. No. 61/651,470 filed May 24, 2012. The full disclosure of which is incorporated herein by reference it its for all purposes.

The subject matter of the present application is related to that of U.S. application Ser. No. 12/261,347 filed Oct. 30, 2008 (now U.S. Pat. No. 8,337,382), entitled "RADIOSURGICAL NEUROMODULATION DEVICES, SYSTEMS, AND METHODS FOR TREATMENT OF BEHAVIORAL DISORDERS BY EXTERNAL APPLICATION OF IONIZING RADIATION;" the full disclosure of which is also incorporated herein by reference in its entirety for all purposes.

BACKGROUND OF THE INVENTION

The present invention is generally directed to medical (and in many cases, more specifically to neurological) treatment devices, systems, and methods. In exemplary embodiments, the invention provides radiosurgical treatment methods and systems for directing ionizing radiation toward a target tissue within a brain of a patient so as to treat psychiatric conditions, and particularly to treat anxiety disorders (such as Post-Traumatic Stress Disorder (PTSD), Generalized Anxiety Disorder (GAD), Panic Disorder, Social Phobia, Specific Phobia, and the like). The dose of radiation will generally be sub-lethal so that the tissue within the target need not undergo frank cell death, with efficacy often instead being provided via radiomodulation of neural activity.

Behavioral disorders, also known as "psychiatric disorders" and "functional disorders," are neurologic and psychiatric conditions that stem from defective regulation of certain brain regions. Patients that suffer from behavioral disorders often exhibit abnormal neural activity along a particular neural circuit within the brain. Typically, areas within the neural circuits of the brain of a behavioral disorder patient are either over-active or under-active, even though the cells of the tissue appear histologically normal. This class of pathology contrasts with structural disorders, in which there is something morphologically or identifiably and physically abnormal with a tissue, such as an injury or a cancerous tumor. Nonetheless, the impact of behavioral disorders, including depression, OCD, addiction, and the like, can be devastating on the lives of patients and their families.

In neurology and psychiatry, behavioral disorders are most often treated with medications. Unfortunately, these medications are often not effective, and can often be non-specific as to where they exert effects within the body. Hence, medications for treatment of behavioral disorders often produce undesirable side effects.

Attempts are being made to treat behavioral disorders by surgical implantation of treatment devices. These surgical implants typically include stimulating electrodes driven by a pacemaker-like pulse generator unit. For example, abnormal neuronal activity associated with intractable depression may be inhibited by continuously applying localized electrical current using a process called deep brain stimulation. Unfortunately, deep brain stimulation generally involves the invasive placement of electrodes into deep brain structures, along with the subcutaneous implantation of an electrical generator with batteries. Such approaches, however, are expensive, and are generally accompanied by risks associated with the surgery, particularly with the risks associated with surgically accessing and/or violating tissues of the brain for implantation of the electrodes such as bleeding and infection. These approaches can also suffer from device-related risks, including device failure, battery-life limits, and the like.

A variety of both historical and modern techniques seek to treat patients by effectively killing cells within selected areas of the brain. Surgical techniques have been developed that intentionally kill or ablate specific regions of the brain using a variety of devices and energy forms. For example, radiation is a widely used method for inducing cell death and effectively destroying tissue within the brain. Radiation is primarily applied to tissues of the brain to treat benign and malignant tumors. The clinical practice of irradiation to produce selective cell death and/or stop growth in tumors generally makes use of computerized systems that seek to minimize injury to adjacent normal anatomy. The biologic effects of radiation can be dose and volume dependent, and are largely ascribed to lethal chromosomal injury which results in disruption of the normal cell cycle. Non-chromosomal, i.e. epigenetic, pathways of cell injury are also believed to play a role in cellular death under some circumstances. Even lower doses of ionizing radiation can induce epigenetic changes that permanently or semi-permanently alter tissue function in the absence of cell death.

While inducing necrosis of selected tissues of the brain can be well worthwhile to halt growth of a malignant tumor or the like, there can be significant and even debilitating side effects, particularly when the tissues targeted for treatment are associated with higher cognitive functions. For example, targeting of apparently healthy tissues of the hyperactive or hypersensitive neural circuits associated with depression, addiction, OCD, or other behavioral disorders with cellularly lethal doses of radiation might effectively treat the disorder, but may significantly degrade cognitive abilities, induce neurological side-effects, and impact quality of life of the patient.

In addition to currently recognized neural circuits associated with behavioral disorders, there is an increasing awareness that abnormal neural activity within the neural circuits of the brain may be associated with a variety of deleterious behavior patterns. For example, while obesity is not uniformly recognized as a class of psychiatric behavioral disorder, there is increasing understanding that hyperphagia (excessive appetite and consumption of food) can be associated with excessive activity in an associated neural circuit. Similar deleterious behavior patterns and their associated anatomical structures within the brain are likely to be identified in the future.

In light of the above, it has recently been proposed to treat behavioral disorders, obesity, and the like by irradiating neural tissues of the circuits associated with those disorders with sub-lethal doses of radiation so as to modulate the activity of those circuits. These proposed therapies present tremendous advantageous, but as with many exciting advancements, still further innovations would be beneficial. Specifically, Post Traumatic Stress Disorder (PTSD) and other anxiety disorders have received more and more clinical attention in recent years. The effects of these anxiety disorders may range widely, and a number of alternative therapies that have been proposed has been expanding. Nonetheless, the individuals with these conditions continue to suffer, even when their behavior remains within societal norms. Hence, it would be desirable if new treatment techniques could be developed help mitigate the debilitating effects of anxiety disorders without imposing excessive surgical trauma on the patient, without subjecting the patient to drug regiments and/or having to damage or kill neural tissues that result in loss of significant cognitive, emotional, or physical functionality to the patient. It would be particularly desirable if these benefits could be provided at reasonable costs by modifying existing treatment infrastructure and technologies.

BRIEF SUMMARY OF THE INVENTION

The present invention generally provides improved medical systems, devices, and methods. Exemplary embodiments of the invention provide improved radiosurgical techniques and systems, particularly for treatment of anxiety disorders (such as Post-Traumatic Stress Disorder (PTSD), Generalized Anxiety Disorder (GAD), Panic Disorder, Social Phobia, Specific Phobia, and the like). Advantageously, radiation can be directed from a radiation source outside the patient toward a target tissue deep within the patient's brain using a stereotactic radiosurgical platform, typically without having to impose the surgical trauma associated with physically accessing deep brain tissues. The target will often include at least a portion of the amygdala, with exemplary treatments being directed to targets that are limited to a sub-region of the amygdala. Rather than applying sufficient radiation to kill the neural tissue within the target, a cellularly sub-lethal dose of the radiation may be applied. Without imposing frank cell death throughout the target, the radiation can mitigate the anxiety disorder, obesity, or the like, often by modulating the level of neural activity within the target and in associated tissues.

In a first aspect, the invention provides a method for treating a psychiatric anxiety disorder of a patient. The disorder will generally be associated with a level of localized neuronal activity within a brain of the patient, as well as deleterious anxiety by the patient. The method comprises identifying a portion of an amygdala on at least one side of the brain of the patient associated with the disorder, and transmitting a cellularly sub-lethal quantity of ionizing radiation from outside the patient selectively into the identified portion of the amygdala of the brain of the patient. The transmission of radiation will be performed so as to alter the level of neuronal activity such that the anxiety of the patient is mitigated.

In many embodiments, the portion of the amygdala will be within a basolateral complex of nuclei within the amygdala. The portion may comprise a sub region included within a limited portion of discrete tissue structures of the amygdala such that at least a region of a boundary of the portion is disposed within, and separate from, anatomical boundaries of the amygdala. The ionizing radiation may be transmitted from a radiation source as a plurality of radiation beams, and further comprising planning the radiation beams so that radiation outside the portion drops off sufficiently to inhibit collateral damage to adjacent neural tissues of the amygdala. The portion of the amygdala targeted by the radiation may have a volume of about 1000 $mm^3$ or less, typically being about 150 $mm^3$ or less, and in some embodiments being about 50-100 $mm^3$ or less, so that many targets may be in a range of volumes of about 50-1000 $mm^3$ For example, the targeted portion may have a volume of approximately 150 $mm^3$, in the case of the centromedial (CeM 802) portion of the amygdala, and approximately 1000 $mm^3$ in the case of the basolateral portion of the amygdala. The large volume associated with the basolateral amygdala may present challenges to treating patients at that location due to the high doses associated with a large volume. Consequently, it may be that better targets for some therapies include volumes that are significantly smaller, such as volumes of less than 500 $mm^3$ (optionally being, for example, about 50-500 $mm^3$) such as the centromedial portion (CeM). Another potential target is the Central nucleus (Ce) of the amygdala, which may be smaller than the BLA, but larger than the CeM. Collimating at least some of the radiation beams to a beam cross-sectional size of less than 5 mm may facilitate targeting the desired portion of the amygdala.

In many embodiments, it may be beneficial to clinically determine that the disorder falls within an accepted psychiatric standard before transmitting the radiation, and/or to verifying that the anxiety is mitigated per a clinical evaluation after transmitting the radiation. Identifying and/or verifying the portion of the amygdala is appropriate for targeting may be performed by imaging differing localized neuronal activity levels within regions of the amygdala of the patient with functional brain imaging modalities including PET, SPECT and fMRI. The sub-lethal quantity of radiation may provide, during a single treatment, a dose in a range from about 25 Gy to about 100 Gy, depending upon the volume to be irradiated, within and/or throughout the portion, optionally being in a range from about 50 Gy to about 70 Gy. The disorder may include Post-Traumatic Stress Disorder (PTSD), Generalized Anxiety Disorder (GAD), Panic Disorder, Social Phobia, and or Specific Phobia.

In another aspect, the invention provides a method for treating chronic post-traumatic stress disorder (PTSD) of a patient. The method comprises transmitting a cellularly sub-lethal quantity of ionizing radiation from outside the patient, through a plurality of intermediate tissues, and selectively into an amygdala of a brain of the patient so as to alter neuronal activity, without surgically accessing the amygdala, such that the PTSD is clinically mitigated.

In a system aspect, the invention provides a system for treating a psychiatric anxiety disorder of a patient. The disorder will often be associated with a level of neuronal activity within a brain of the patient and provoking deleterious anxiety of the patient, and the system may comprise a source for transmitting ionizing radiation. A processing system is coupled to the source, and the processing system can be configured to effect transmission of a plurality of beams of the radiation from the source selectively into an amygdala within the brain of the patient so that the radiation within the amygdala is cellularly sub-lethal, and is sufficient to alter the level of neuronal activity such that the anxiety associated with the disorder is clinically mitigated.

Optionally, the processing system may include software, with the software comprising tangible media with non-volatile machine-readable code embodying instructions for planning transmission of the plurality of beams in response to input command signals received by an input. The processing system may transmit signals per the software so as to effect a desired positioning of the radiation beams relative to the brain of the patient.

In another aspect, the invention provides a system for treating chronic post-traumatic stress disorder (PTSD) of a patient. The system comprises a source for transmitting ionizing radiation, and a processing system coupled to the source. The processing system may be configured to effect transmission of a plurality of beams of the radiation from the source from outside the patient, through a plurality of intermediate tissues, and selectively into an amygdala of a brain of the patient so as to alter neuronal activity, without surgically accessing the amygdala, such that the PTSD is clinically mitigated.

The amygdala may be included in a neural circuit associated with the disorder, and the neural circuit will typically comprise a recognized neural circuit associated with a specific clinical disorder. A variety of such neural circuits are now known, and more are being developed through the use of imaging techniques which can indicate local neuronal activity levels within the tissues of the brain. Although the overall functioning of the neural circuit is often abnormal prior to treatment of a behavioral disorder patient (for example, with abnormally excessive neuronal activities in some or all of the neural circuit) the neural tissue within the target will often be morphologically normal prior to the treatment, so that the treatment is directed at what may be effectively healthy tissue. At the same time, a level of activity in a given brain region may be normal in the statistical sense, but inappropriate to achieving balance in a brain circuit. That is to say, a based on the needs of proper functioning of a circuit as a whole, the activity level of a given node may desirably be reduced. Nonetheless, by selecting an appropriate target within the neural circuit, and by applying a quantity of radiation that is sufficient to decrease the level of neuronal activity within the targeted neural tissue (but which is insufficient to generally kill the tissue of the target), the level of overall activity of the neural circuit may be safely and effectively decreased without excessively (or even noticeably) impairing the higher cognitive, emotional, and/or physical functioning of the patient. Alternatively, where the neural tissue within the target down-regulates the level of neuronal activity within at least a portion of the neural circuit, the radiation may decrease activity in the neural tissue and lead to an increase in the level of neuronal activity within some or all of the neural circuit.

In some embodiments, the target may comprise one or more discrete tissue structure of the brain having anatomical boundaries. The ionizing radiation can be transmitted from a radiation source as a plurality of radiation beams, and the radiation beams can be planned so that radiation outside the anatomical boundaries drops off sufficiently to inhibit collateral damage to adjacent neural tissues and preserve cognitive function. As the dosage of radiation even within the target neural tissue is generally cellularly sub-lethal, effects outside the anatomical boundaries of the target may be quite limited or even negligible. The volume of the target will often be quite small, the target typically having a volume of less than 100 mm$^3$, often having a volume of less than 125 mm$^3$, and in some cases having a volume of less than 0.50 mm$^3$. To facilitate treatment of these small tissue volumes and minimize collateral tissue damage, some or all of the radiation beams may be smaller in cross-section than those used in standard tumor-treatment stereotactic radiosurgery. For example, at least some of the radiation beams may be collimated to a beam cross-sectional size of less than 3 mm.

Before treatment, a medical professional will typically clinically determine that the disorder falls within an accepted psychiatric standard. Such standards may, for example, comprise one or more of those included within the Diagnostic and Statistical Manual of Mental Disorders, 4th edition ("DSM IV"), or the DSM 5 and other volumes regarding official psychiatric disorder classification criteria that will succeed it. The target may be identified using an accepted psychiatric neural circuit associated with the behavioral disorder of the patient. The target may also be identified, verified, and/or tailored by imaging localized neuronal activity levels along the neural circuit of the patient. Hence, for example, once a clinical diagnosis is established and the patient otherwise meets the patient selection criteria, relative hyperactivity of a candidate neural circuit known to be associated with the disorder can verify that the treatment is appropriate, and the radiation beam trajectories can be planned based on the anatomical borders of the discrete tissues of the particular patient. Imaging may also be performed an appropriate tissue response time after treatment and to verify that sufficient neuromodulation has been provided, to determine whether a follow-on treatment is appropriate, and/or to plan that follow-on treatment in a fractionated treatment regime. It may be advantageous to verify mitigation of the disorder after more than a month, and often after at least two months, as the changes in the level of neuronal activity may continue for at least a period of weeks or months after the radiation has been delivered to the target.

The sub-lethal quantity of radiation may depend at least in part on the volume of a discrete region of the target tissues. For example, the radiation dose for a single treatment may comprise about 65 Gy when the target has a volume of about 0.05 cc (and more specifically when the target has a volume of about 0.054 cc). In contrast, the radiation dose may be significantly less than about 65 Gy when the target has a size of significantly more than about 0.05 cc, and/or more than about 65 Gy when the target has a size of significantly less than about 0.05 cc (such as when the target has a volume of about 0.01 cc or less). For example, targets in various embodiments for the treatment of anxiety may have volumes between 150 mm$^3$ and 1000 mm$^3$, although only a portion of the potential target volumes may be treated in some cases (particularly when the overall target structure is relatively large).

The software may, in response to input command signals received by the input, transmit signals so as to effect a desired positioning of the radiation beams relative to the target, the signals typically comprising drive signals that effect movement of the source, the patient, or both. The system may include a neural circuit image capture device coupled to the processing system. The image capture device may, in use, generate image data that includes localized neuronal activity levels along the neural circuit in the brain of the patient, the image capture device coupled to the processing system. Suitable image capture devices may include a positron emission tomography (PET) system, a single photon emission tomography (SPECT) system, and/or functional magnetic resonance imaging (fMRI) system.

In some embodiments, the source may comprise a linear accelerator. The processing system can be configured to generate a sequence of beams, and a robot may be coupled to the processing system and support the source. The robot may re-position the source and orient sequential beams toward the target tissue. One or more registration imaging system may be oriented to obtain patient registration images of the patient during treatment. The registration imaging system will typically be coupled to the processing system, and the processing system may align the beams with the target (often in three dimensions) in response to registration signals from the registration image system. In alternative embodiments, the source may comprise a plurality of cobalt 60 sources distributed generally spherically, with an associated plurality of collimators oriented generally radially inwardly so that at least some of the beams are simultaneously directed toward the target.

DETAILED DESCRIPTION OF THE INVENTION

Figure 1:
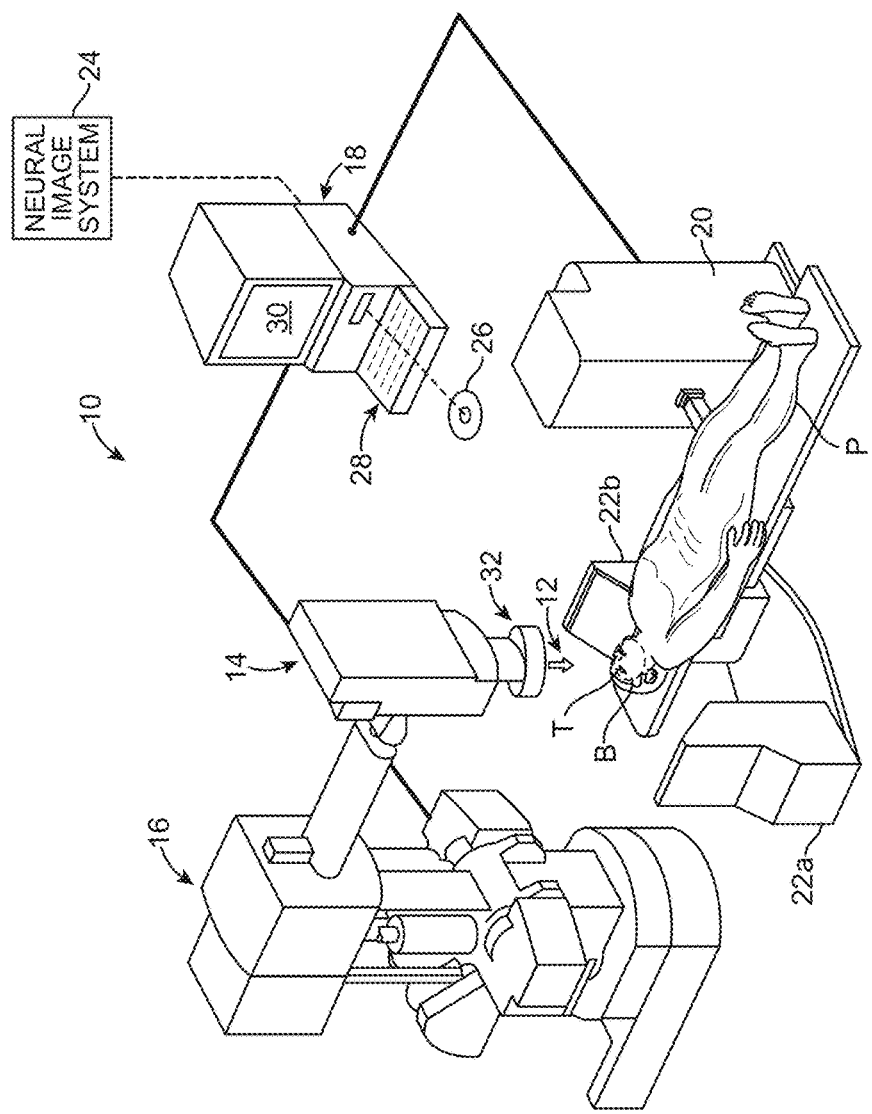
FIG. 1 schematically illustrates components of a robotic stereotactic radiosurgical system and an associated method for applying cellularly sub-lethal ionizing radiation to a target within a brain of a patient so as to treat a behavioral disorder, hyperphagia, obesity, or the like, according to embodiments of the invention.

The present invention generally provides improved medical systems, devices, and methods. Exemplary embodiments of the invention provide improved radiosurgical techniques and systems, often to treat anxiety disorders through selective targeting of the amygdala's basolateral complex of nuclei (abbreviated BL). Pathological over-activity in one, some, or all of these radiosurgical neuromodulation targets may have specific anxiety disorder behavioral disease symptoms associated with them.

Embodiments of the invention may be based on systems and methods developed for treatment of behavioral disorders, including depression, Obsessive-Compulsive Disorder ("OCD"), and addiction. Treatments are also provided for additional medical and/or psychiatric conditions, particularly those that are associated with neural activity levels in identifiable neural circuits of the brain, including hyperphagia and obesity. As treatments described herein may rely on the delivery of radiation transmitted from a source outside the patient, through the skull and any intervening tissues, and concentrated within the target, these treatments may optionally avoid the surgical trauma associated with accessing deep brain tissues. Alternative embodiments could, however, combine non-invasive methodologies described herein with minimally invasive or even traditional open surgical techniques. While some embodiments might employ sufficient radiation to result in significant necrosis within (or even throughout) the target, exemplary embodiments will generally limit the radiation to cellularly sub-lethal dosages, so that there will be little or no necrosis. Frank cell death will typically be limited or absent, but the radiation will modulate, and typically decrease the overall level of neuronal activity within the target. By down-regulating the activity of a target that normally exerts negative feedback or a limiting effect on another neural tissue, neural activity may alternatively be increased.

Advances in brain imaging, especially those involving MRI and PET, are starting to unravel a spectrum of psychiatric behavioral disorders. Such imaging modalities have implicated a number of specific anatomic regions as being involved in some pathologic brain conditions. The altered imaging characteristics of these regions may allow physicians to visualize the brain pathology that underlies diseases such as depression and addiction. In a more specific example, treatment-resistant depression may particularly benefit from the treatments described herein. Increased metabolic activity in Brodmann's Area 25 may correlate well with clinical depression. This anatomical structure may also interact with a variety of other anatomical structures having altered activity levels in many patients suffering from depression, with the interrelated tissue structures generally defining an abnormally functioning neural circuit model. Using these imaging techniques and/or the neural circuits that have been identified for specific behavioral disorders, the effects of therapy for those behavioral disorders may be monitored by means of MRI and PET.

The neural tissues targeted for the radiation treatments described herein will often be included within an abnormally functioning high-level neural circuit of the patient's brain. Also, function of this brain region may be high only in the relative sense, in that reduction of even a typical level of activity may appropriately change the output of the brain circuit as a whole. In some cases, the target may not be in the neural circuit itself, but may functionally interact with a tissue included in the neural circuit, with activity in the target effectively up-regulating activity. A variety of neural circuits are known to be associated with individual behavioral disorders. Exemplary neural circuits associated with depression, Obsessive-Compulsive Disorder ("OCD"), addiction, and obesity are described herein, and these exemplary circuits may be used to identify appropriate tissues to target for patient having these disorders or conditions. The invention is not, however, limited to the specific behavioral disorders and/or neural circuits provided herein, as additional and more refined neural circuits are (and will continue to be) developed.

In some embodiments, the overall neural circuits associated with the disorder may also, at least in part, be determined, refined, and/or verified by appropriate imaging of a specific candidate patient suffering from a disorder. In some embodiments, hyperactivity along a neural circuit may be seen in a patient having an acute or ongoing episode by imaging the neural tissues with imaging modalities that indicate localized neuronal activity levels. For example, by stimulating the brain of a patient with an addiction with associated drug paraphernalia images or the like, the neuronal activity may be imaged and measured along an addiction neural circuit to verify that particular neural circuit model is applicable to the patient, to verify that a candidate target neural tissue becomes hyperactive during the episode, and to tailor the target shape to the anatomical boundaries of the patient's brain physiology. Treatments may be fractionated, with follow-up clinical diagnosis and/or imaging after at least one treatment to determine whether additional modulation of the same target is appropriate, to select additional targets, or to determine that treatments can be suspended or terminated. More directly, treatments may be repeated if inadequate clinical response has been obtained.

Radiosurgery is an established method for using intense, highly accurate irradiation to non-invasively ablate (killing, otherwise destroying, or to halting the physical growth of) abnormal tissue within the body, for example, brain tumors. Examples of radiosurgical platforms include the Cyberknife (Accuray, Inc., Santa Clara, Calif.), the Gamma Knife (Elekta, Stockholm Sweden), and the Trilogy System (Varian, Palo Alto, Calif.). These or other commercially available radiosurgery systems may be modified to take advantage of the inventions described herein, or specialized radiosurgical systems for treatment of behavioral disorders may be employed.

The present invention often applies radiosurgical platforms for neuromodulation rather than ablation. Radiomodulation ("RM") (also referred to herein as radiosurgical neuromodulation) encompasses the use of non-necrosing stereotactic radiosurgery for the down-regulation of activity in selected neural structures. Advantageously, small and strategically important neuronal regions may be treated with dosages of radiation that are sufficiently low to leave their tissues alive and functional, but are sufficiently high to make them less functionally reactive, and less able to trigger action potentials, i.e. precipitate deep-brain neuromodulation clinical response. A variety of data may be applied to identify appropriate dosages to alter brain function without frank cell death. Irradiation of the entire brain of patients produces long-term cognitive decline without producing clear evidence of tissue necrosis, and may produce other undesired emotional and physically-manifested neurological symptoms. Decreased neuronal excitability within hippocampal slices of pig brain has been revealed by in vitro evidence. Moreover, treatment of trigeminal neuralgia with radiosurgery has been found to provide symptom relief that does not correlate temporally with facial numbness. In fact, treatment of more than 100 patients with refractory trigeminal neuralgia has shown that the complete remission of pain occurs in a setting of essentially normal facial sensation. Dose application rates may alter the total dosages to achieve a desired result. At dose rates of 20 Gy per minute, synaptic damage (lessened ability to transmit excitation to another neuron) may occur when a 50 Gy total dose had accumulated. Doses of 75 Gy and greater may provide both synaptic and postsynaptic damage (lessened ability of a downstream neuron to produce an action potential). At slower delivery rates of about 5 Gy/min, however, a total dose of 100 Gy or more may be applied to induce synaptic impairment, while post-synaptic impairment may not be dose-rate dependent. Appropriate dosages may also vary with the inverse of a volume or size of the target. One exemplary treatment of a target volume of about 3 mm by about 3 mm by about 6 mm (about 0.054 cc) will employ a dosage of about 65 Gy to achieve RM; significantly larger target volumes may employ lower dosages; while smaller target volumes may employ significantly higher dosages.

While many embodiments do not rely on any particular mechanism or theory of operation, ionizing radiation may cause an inhibitory effect upon voltage-sensitive sodium channels in the brain. This may results in a state in which affected neurons remain chronically in a hyperpolarized state, which is resistant to depolarization. Radiation may also result in the thickening of blood vessel walls and narrowing of lumens, to the point of frank destruction of the microvasculature, leading to reduced blood delivery capacity within an irradiated area or frank destruction of oligodendrocytes. These effects may be progressive over time after radiation exposure, reaching a steady state. Radiation may cause the disruption of myelin sheathing and consequent reduced efficiency of axonal transmission. Increases in astrocytes and microglia may change synaptic behaviors. Additionally, the blood-brain barrier may be disrupted by ionizing radiation, allowing release of neuromodulatory substances such as neurotensin, histamine and serotonin. Hence, moderate-dose radiation may alter neuronal and synaptic activity through mechanisms that change the functional characteristics of individual cells without killing those cells. By physiologically altering, but not destroying, discrete neural circuits, brain activity can be modulated.

Regardless of brain target, one mechanism by which radiosurgical neuromodulation may biologically exert its intended effect is, at least in part, by inducing alterations in the glial cells which surround the neurons. Glia may not only support and surround neurons in the brain, they likely regulate synaptic connectivity. In the months that follow irradiation, a reactive astrocytosis and microglial changes may occur with in increased numbers of such cells in the irradiated area more densely surrounding the neurons in the same region, particularly astrocytes and microglia. Reduction of myelin sheathing extending from oligodendrocytes and ensheathing neuronal axons may also be affected.

Specifically addressing the of treatment anxiety disorders, there are similarities and differences among a variety of anxiety disorders in human patients, including patients with Post Traumatic Stress Disorder (PTSD), social anxiety disorder (SAD), specific phobias (SP), and/or experimental fear conditioning. Despite distinct differences in the activity of various parts of the brain in various anxiety disorder conditions, a common denominator of many may be increased amygdala activity. Specifically, human amygdala activity levels are abnormally high in patients with post-traumatic stress disorder (PTSD), social anxiety disorder (SAD), specific phobias (SP) and experimental fear conditioning. The amygdala is a portion of the brain inside the temporal lobes on each side of the brain. This area can be associated with fear and aggression. Electrical stimulation of this structure via deep brain stimulation electrodes is sometimes associated with rage reactions in animal subjects. Procedures in which one or both amygdalae are surgically destroyed can produce inconsistent results, particularly where the amygdala is treated as a monolithic structure and the end goal of the procedure is the production of a destructive lesion (in other words, purposely killing brain cells and parts of the brain).

Less destructive surgical treatment of the amygdala in laboratory animals may provide beneficial results. Deep Brain Stimulation (DBS) structures placed in the basolateral (BL) nucleus of laboratory rats in an animal model of post-traumatic stress disorder (PTSD), followed by application of high-frequency DBS stimulation may result in greatly reduced pathological fear-related behaviors exhibited by those rats during test periods following the basolateral amygdala stimulation. Additional details on such treatments and their results may be understood with reference to Langevin J P et al.'s article "Deep Brain Stimulation of the Amygdala Alleviates Post-traumatic Stress Disorder Symptoms in a Rat Model; J Psychiatr Res. 2010 December; 44(16):1241-5. Epub 2010 May 26. Optogenetic stimulation methods triggered by surgically implanted optical fibers which delivered light to the basolateral nucleus nerve terminals residing in the central nucleus of the amygdala have similarly been shown to produce reversible and bidirectional control of anxiety behaviors in laboratory mice. The central amygdala (Ce), particularly its medial sector (CeM), may be the main output station of the amygdala for conditioned fear responses. Ce lesions may block the expression of conditioned fear-based freezing behavior in laboratory animals. Fear conditioning may causes many CeM neurons to increase their responsiveness to fear-invoking stimuli. These responses may disappear with the extinction of conditioned fear.

Knowledge of human amygdala anatomy has lagged behind understanding of animal brains, and the general expectation is that there will be some differences. Delgado and colleagues have confirmed that in humans fear produces increases in amygdala activity, while interventions that result in extinction (loss of) of fear decrease amygdala activity. In the normal state, the human basolateral nucleus complex (BL), central nucleus complex (Ce), and the Ce-derived centromedial nucleus (CeM) are major sites of communication inflow and outflow that govern anxiety-related disorders. BL chiefly communicates with cortical regions of the brain, partially via the thalamus, and are associated with conscious perceptions of fear. The Ce and the CeM send signals chiefly to subcortical regions of the brain to facilitate autonomic reactions of the body. In nature, these body responses serve principally defensive roles—for example "fight or flight" responses that are critical for survival. In the pathological state, however, excessive signals emanating from an overactive Ce, CeM or BL may manifest as fear, racing heartbeat, sweating, cold hands, or GI tract pain or dysfunction. The strength of these connections to and from the amygdala nuclei, however, has been shown to exhibit significant variability from person to person in terms of the strength or even the presence or absence of these amygdala connections. Detailed functional MRI brain imaging studies of the amygdala in the context of normal subjects, and those with anxiety disorders (by Etkin et al.) have indicated that the connectivity patterns in the basolateral nuclear complex, central nucleus and the centromedial nucleus is weaker in those with anxiety disorders than in normal control subjects without anxiety disorders. Accordingly, hypermetabolic states in amygdala subregions can have widespread and severe consequences in the form of anxiety disorders. Increasingly sophisticated methods for visualizing the separate nuclear complexes that comprise the amygdala are being developed. For example, the ultra-high resolution MRI methods of Entis and colleagues now make it feasible to identify in 3D space not only the amygdala, but also its major subregions.

Referring now to FIG. 1, an exemplary stereotactic radiosurgery system 10 for treatment of an anxiety disorder, a behavioral disorder, or hyperphagia of a patient P directs ionizing radiation 12 to a target T in a brain B of the patient. System 10 includes a linear accelerator 14 supported by a 6 degree of freedom robot 16, which allows the linear accelerator to be moved around the patient, so that radiation 12 can be directed to target T as a sequential series of beams that pass through different intermediate tissues from a variety of different orientations, thereby limiting the amount of radiation outside the target.

System 10 also includes a processing system 18 that is coupled to linear accelerator 14 to control transmission of radiation 12. Processing system 18 is also coupled to robot 16, and optionally to an automated patient support 20 to reposition radiation 12 relative to the patient P and target T. Processing system 18 may also be coupled to one or more imaging system(s) used for planning of the treatments, to imaging systems 22a and 22b used to register radiation beam 12 with target T in three dimensions and/or track patient movements during treatment. Registration imaging systems, the linear accelerator, the robot, and the patient support may be the same as or modified from commercially available robotic radiosurgical systems, including the CyberKnife radiosurgical system. Additional or modified imaging structures and systems will often be coupled to processing system 18 so as to provide input for planning the treatment and the like, such as a neural activity imaging system 24.

To facilitate treatment of the relatively small volume discrete anatomical structures of the neural circuits, system 10 will typically include a collimator 32 which selectably narrows beam 12 to beam cross-sectional sizes of 3 mm or smaller, and in some embodiments to a cross-sectional size of 5 mm or smaller.

Processing system 18 may include some or all of the components of a commercially available computer system. Processing system 18 will, for example, typically include at least one hardware processor circuit, which may communicate with a number of peripheral devices via a bus subsystem. These peripheral devices may include a memory system, and the memory will typically include a tangible storage media 26 embodying machine (i.e., computer) readable instructions for performing methods (including those described herein) and/or data. The memory may comprise a random access memory (RAM), a read only memory (ROM), a persistent (non-volatile) storage such as a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks including flash RAM.

In some embodiments, processing system 18 will comprise a proprietary structure, and will likely include a plurality of discrete processing circuits, with separate structures of the processing system being primarily used for planning treatments, analyzing neural images, controlling movement of robotic components of system 10, and the like. Alternatively, simpler systems might employ a single processor chip running a monolithic computer program and packaged with single input 28 and display 30. Hence, a wide variety of centralized or distributed data processing hardware and software architectures may be implemented, and the functionality described herein may be implemented in a variety of software and/or hardware modules distributed in different data processing structures and locations. Exemplary embodiments of the processing system 18 of system 10 may be provided by input to and modifications of the data processing and signal transmission systems of commercially available radiosurgery systems such as the CyberKnife™ robotic stereotactic system from Accuray, Inc.

Figure 2:
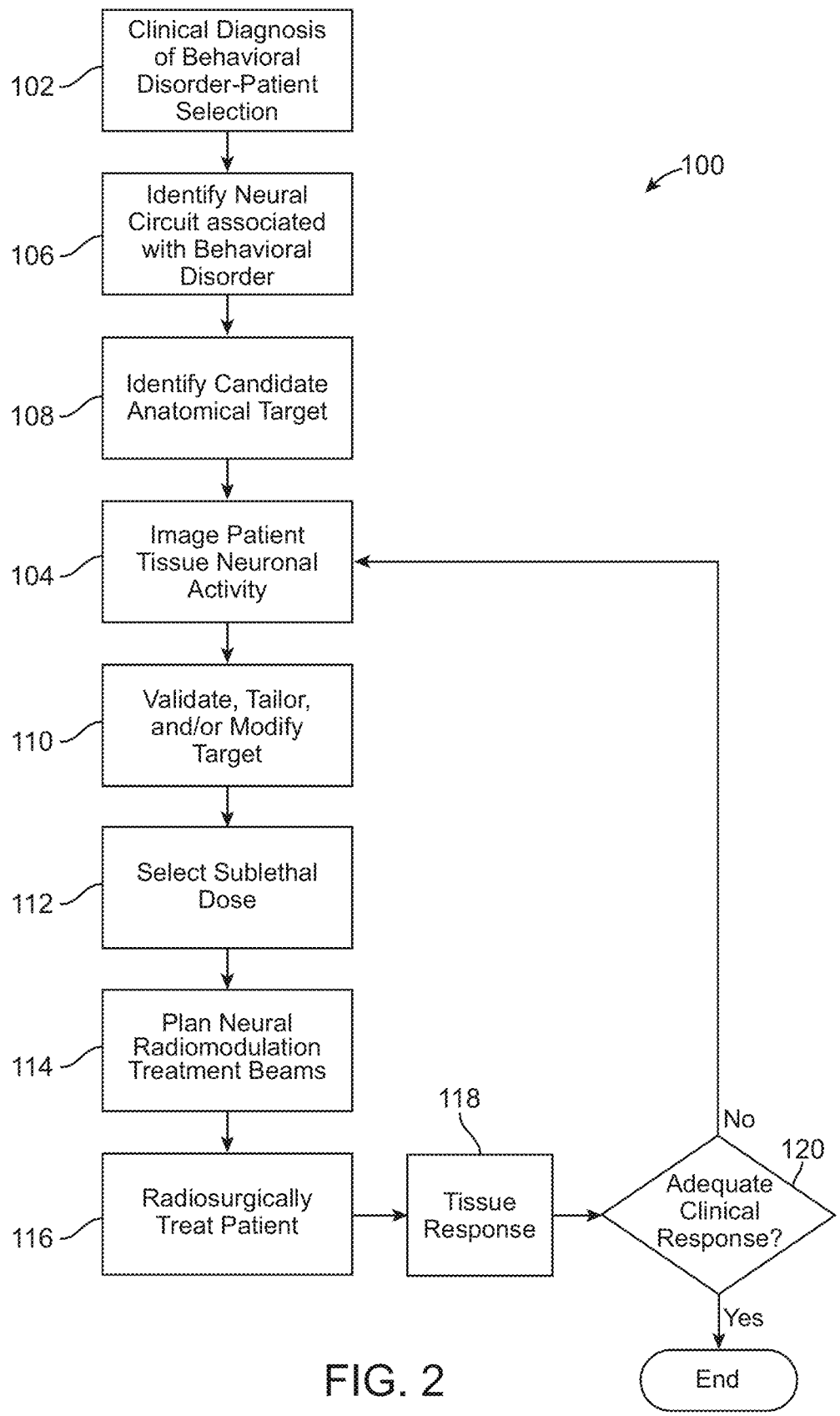
FIG. 2 is a flow chart schematically illustrating steps included in a method for treating a behavioral disorder, hyperphagia, or the like using the system of FIG. 1 or other radiosurgical systems.

Referring now to FIG. 2, an exemplary method 100 for treatment of an anxiety disorder, a behavioral disorder, hyperphagia, obesity, and/or the like will often begin with the selection of an appropriate candidate patient. Such a patient will typically have a neuropsychiatric brain disorder for which there is reason to believe that one or more specific regions of the brain are overactive or hypermetabolic. This diagnosis may be accomplished via clinical judgment 102, and/or may be accomplished with the aid of functional brain imaging 104. In clinically diagnosing an anxiety or other behavioral disorder, a medical professional will typically clinically determine that the behavioral disorder falls within an accepted psychiatric standard. Such standards may, for example, comprise one or more of those included within the Diagnostic and Statistical Manual of Mental Disorders, 4th edition ("DSM IV"). Suitable imaging techniques for behavioral disorder diagnosis will generally indicate localized neuronal activity levels, with exemplary imaging systems optionally comprising positron emission tomography (PET), single photon emission tomography (SPECT) or functional magnetic resonance imaging (fMRI). Imaging of the patient's head preferably involves acquiring both a high resolution MRI scan of the patient's brain and a thin section CT scan of the same region, the latter ensuring spatial integrity in the radiosurgery planning process.

Figure 3:
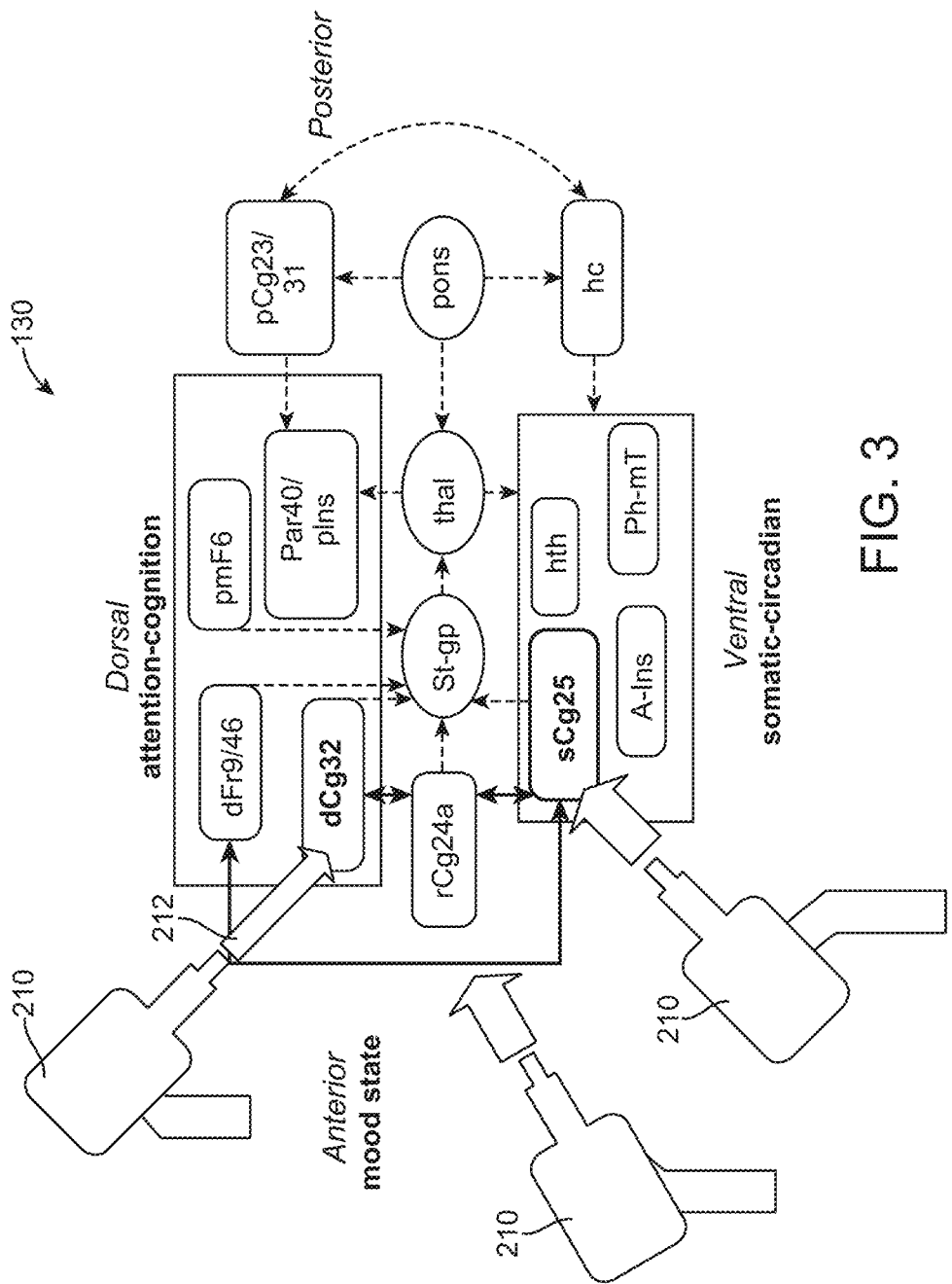
FIG. 3 schematically illustrates a neural circuit associated with depression, along with candidate tissues suitable for treatment according to embodiments of the invention.

Neural circuits associated with the behavioral disorder may be identified 106 before or after imaging 104. Suitable neural circuits may comprise neural circuit models indicating functionally related tissues that have abnormal activity levels, as determined from a population of patients having the associated behavioral disorder. Exemplary neural circuits are shown in FIG. 3 (depression), FIG. 7 (hyperphagia and/or obesity), FIG. 8 (addiction), and FIG. 9 (OCD). One or more candidate anatomical target corresponding with the behavior is identified 108 in the context of the surrounding anatomy using the identified neural circuit 106 and/or the data from imaging 104. The imaging data may be used to verify, tailor, and or modify the candidate target 110. For example, the depression circuit 130 of FIG. 3 may be identified in response to a clinical diagnosis of depression within the DSM IV criteria, and imaging of the patient's brain may verify hyperactivity of subgenual cingulate indicating this is a suitable candidate target. The anatomical boundaries of the target tissue (subgenual cingulate in our example) for the patient may also be identified using the imaging data.

In step 112, a neuronally and/or cellularly sublethal radiation dose is selected. Unlike traditional ablative radiosurgery dosing, the goal in many embodiments of the present invention is explicitly to not destroy the brain tissue effected, but rather to simply lower its reactivity, metabolic activity, and/or spontaneous firing rate. For example, a marginal dose of 65 Gy may be prescribed to the target volume, with a maximum dose at any point of 75 Gy during one treatment stage. The selected dose should be sublethal to neurons, but effective in lowering their activity.

Figure 5:
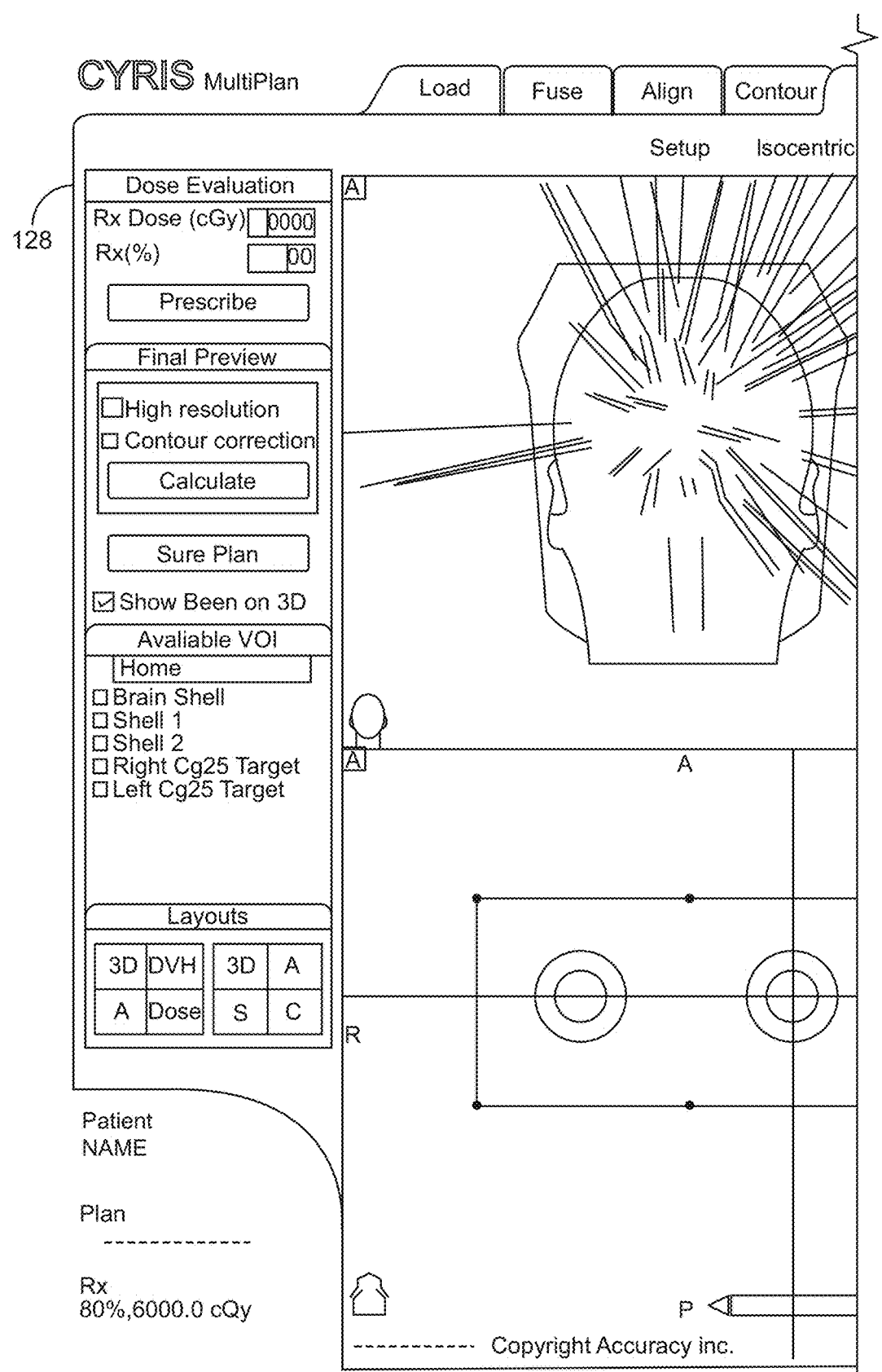
FIG. 5 illustrates a screen print from a planning module included in a processing system of the system of FIG. 1 for implementing a treatment according to embodiments of the invention.
Figure 5:
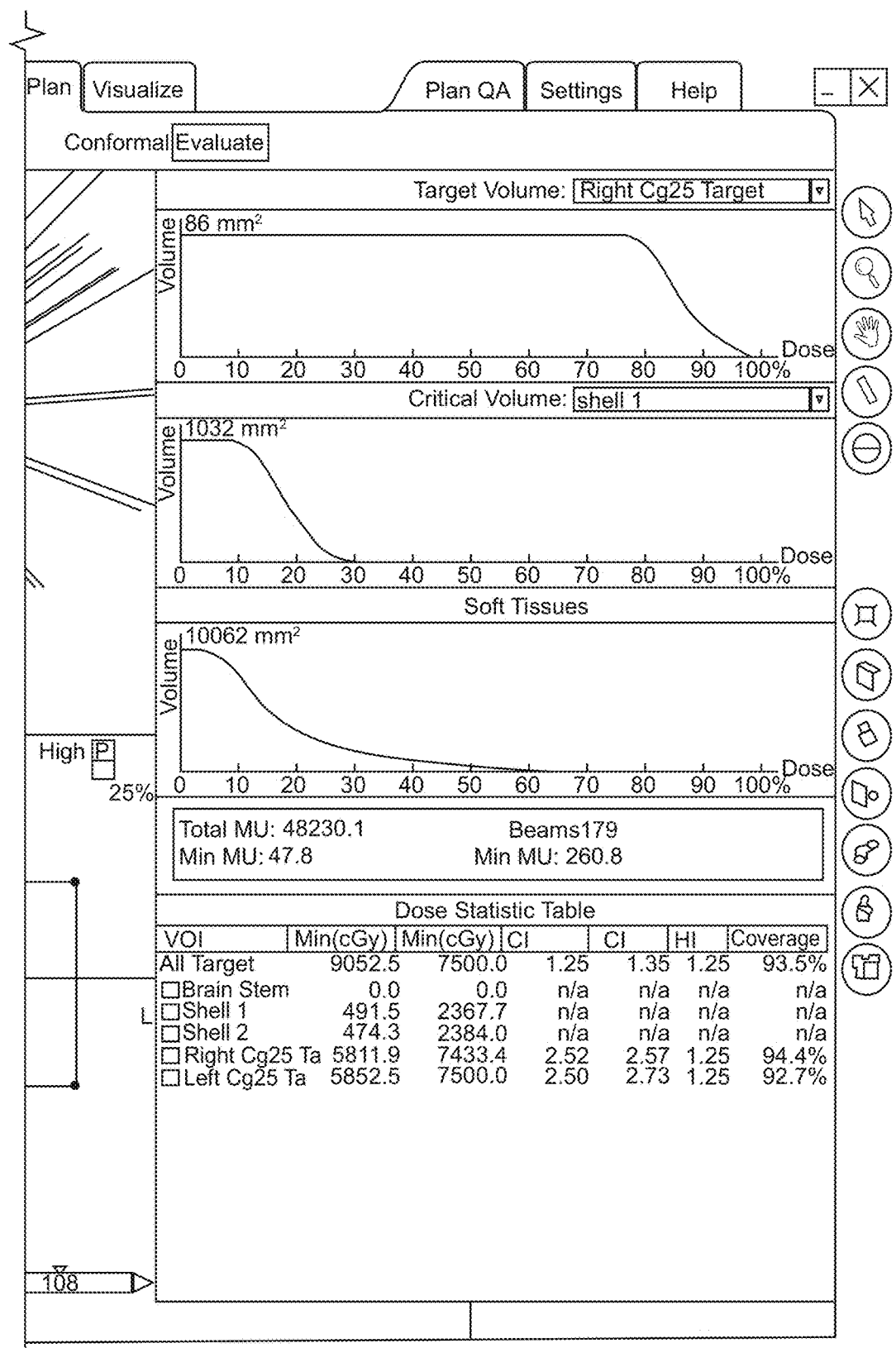

In step 114, preferably using a fused data set of each patient, the radiation treatment is planned. The Cyberknife™ treatment planning interface (or a modified version thereof), may, for example, be used to delineate, an approximately 80 mm$^3$ target volume within the subgenual cingulute. Referring to FIGS. 2 and 5, a screen print 128 of the Cyberknife™ treatment planning interface shows how the system facilitates planning of beam trajectories. The planning system should algorithmically seeks to achieve a steep dose gradient in the immediately surrounding brain. The radiosurgical platform will then compute a set of beam delivery trajectories in order to achieve the prescribed dose. These planning steps will often be performed on a separate computer circuit than that used to control the robot and activate the radiation source, with these separate data processing structures herein being referred to as elements of processing system 18.

The completed plan will be loaded into the treatment circuitry of the radiosurgical platform, for example a Cyberknife system, and the radiomodulation procedure will be performed 116. In the CyberKnife treatment room the patient is positioned supine on the procedure table while immobilized in a custom molded mask. The patient will be registered with respect to the spatial coordinates of the Cyberknife system, using an x-ray camera/CT matching system. Once proper registration has been confirmed, radiation delivery proceeds in accordance with the treatment plan described above, for example, at a marginal dose of 65 Gy (Dmax 75 Gy) is delivered to the subgenual cingulate target. Because radiation effects often manifest a significant time 118 after surgery, a tissue response time of at least a plurality of weeks will pass before evaluation of the effects of treatment 116 is complete. Tissue response times will often be at least a week, more typically being a plurality of weeks, and in exemplary embodiments, may be about one month, so that clinical evaluation 120 of the treatment occurs approximately 30 days following treatment.

In clinical evaluation of the patient 120, the patient is re-evaluated, and may have additional neuroimaging (step 104, repeated) done. Clinical evaluation and/or imaging endpoints may determine whether a second stage of RM treatment is warranted. Criteria for recommending an addition stage of RM may include insufficient clinical response to previous RM stages, absence of sufficient metabolic decrease (for example in subgenual cingulate), and/or absence of significant impairment of surrounding brain structures.

Referring now to FIG. 3, exemplary target neural tissues included in a neural circuit 130 associated with depression are identified using a schematic radiation source 210 and associated radiation beam 212 directed to the target tissues. The solid small arrows shown on this neural circuit diagram schematically illustrate reciprocal corticolimbic, limbic-paralimbic, and cingulate-cingulate connections. The dotted arrows illustrate cortico-striatal-thalamic pathways. The dashed arrows show potential action in which remission to depression occurs when there is inhibition of the overactive ventral regions and activation of the previously hypofunctioning dorsal areas. This effect may be facilitated by antidepressant action in the brain stem, hippocampus, and posterior cingulate gyms. Candidate target tissues of neural circuit 130, as shown in FIG. 3, may include a dorsal anterior cingulate cortex dCg24; a rostral anterior cingulate cortex rCg24a; Cg32; and/or a subcollosal cingulate, sometimes referred to as subgenual cingulate; an area that may include portions of Brodmann's area 25, 24, 32, and 10. An exemplary treatment for depression will, for example, comprise targeting of Cg25. Other tissues included in neural circuit 130 include dorsal prefrontal cortex or dorsolateral prefrontal cortex dFr9/46; parahippocampus-medial temporal ph-mT; premotor frontal cortex pmF6; pariental cortex or posterior insula Par40/pins; striatum-globus pallidus St-gp; thalamus thal; pons; hypothalamus hth; anterior insula A-Ins; hippocampus hc; parahippocampus or medial temporal lobe Ph-mT; and posterior cingulate cortex pCg23/31. Additional information regarding related neural circuits is available from a number of sources, including the publications of Helen Mayberg and others. In some embodiment, the medial forebrain bundle may be included as a potential target for mitigation of depression, and particularly the RM of the medial forebrain bundle.

Figure 4B:
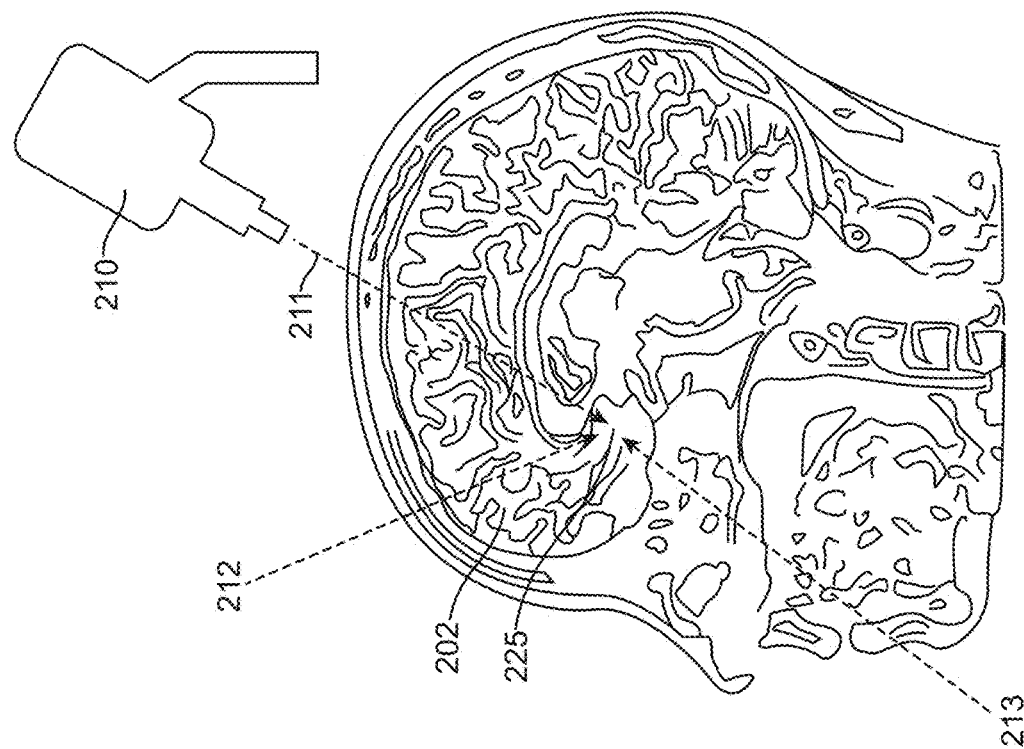
FIGS. 4A and 4B schematically illustrate a patient having target neural tissues at the subgenual cingulate irradiated for treatment of depression according to an embodiment of the invention.
Figure 4A:
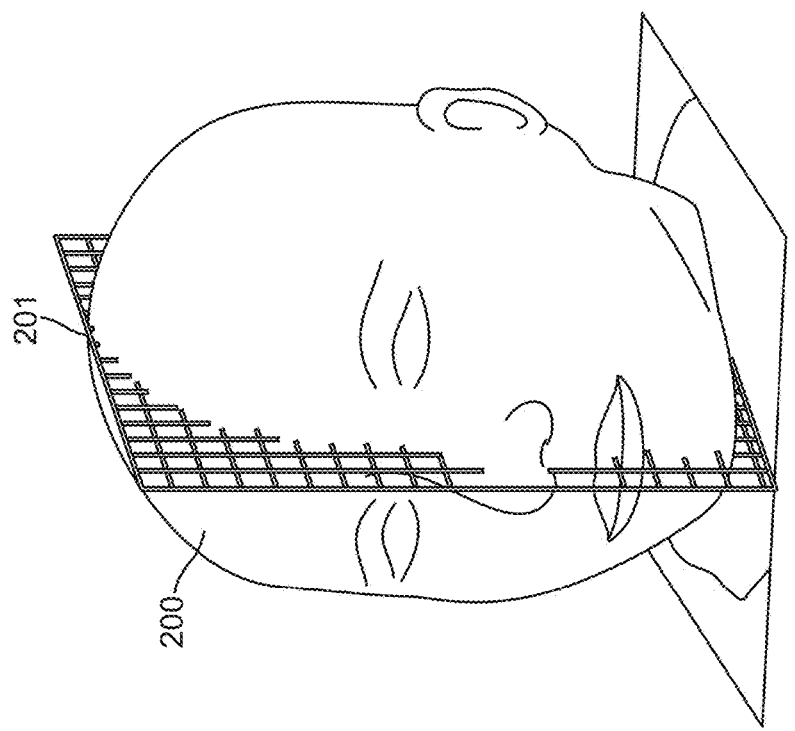

Referring now to FIG. 4A and 4B, patient's head 200 is illustrated in cross-section along plane 201. Within brain 202, subgenual cingulate target 225 (subgenual cingulate) is visible. Radiation source 210 is schematically illustrated delivering a beam along trajectory 211, and will also be used (by robotically moving the source) to direct radiation along trajectory 212, and trajectory 214, all of which intersect at target 225. The total dose of radiation to be received by target 225 downwardly modulates target 225 reactivity, metabolic rate, and/or spontaneous firing rate, but does not tend to ablate or destroy the tissue (Cg25) within the target.

Referring to FIG. 5, a screen shot 128 of an interface for planning of a RM treatment for mitigation of a behavioral disorder per the system user input is shown. Screen shot 128 may also indicate gradients of radiation to which adjacent neural tissues are subjected, as well as the trajectories of radiation beams generated by the software. Tissues which are desired to have particularly limited radiation may also be identified by the input from the system user, so that the system calculates appropriate trajectories to limit collateral tissue damage of sensitive structures.

FIGS. 6A-6C and 7 illustrate a process by which obesity and/or hyperphagia may be treated and a neural circuit associated with obesity. In the exemplary method obesity and excessive eating disorders may be treated by radiomodulation of the lateral nuclei of the hypothalamus. The nuclei of the lateral hypothalamus, which comprises the lateral hypothalamic area, is a portion of the brain which creates the sensation of hunger. For example, when the blood sugar level declines, this message is relayed to the lateral hypothalamic area, which then causes a sensation of hunger to be felt. This feeling will continue until adequate glucose in the blood signals the ventromedial nuclei of the hypothalamus, which creates a sensation of satiety. Damage to the lateral hypothalamic area can lead to reduced food intake. High-frequency deep brain stimulation, which typically has an inhibitory effect upon stimulated structures, leads to a similar reduced appetite state. In this embodiment, obesity treatment may instead be provided using radiomodulation to the lateral nuclei of the hypothalamus, typically on each side of the brain.

Figure 6A:
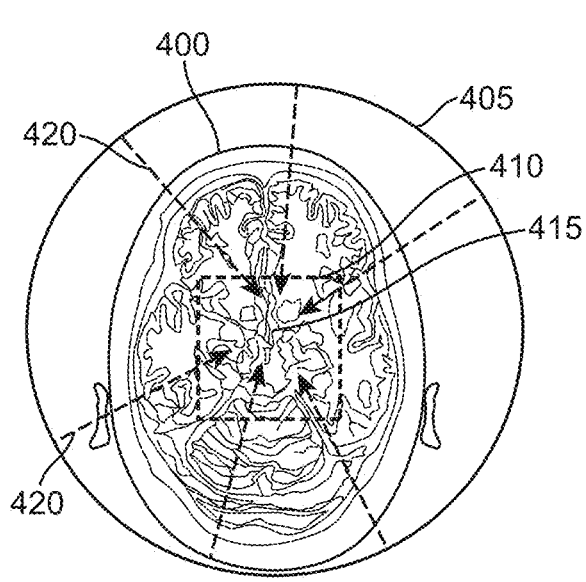
FIGS. 6A-6C graphically illustrate exemplary target neural tissues for treatment of obesity according to embodiments of the invention.
Figure 6B:
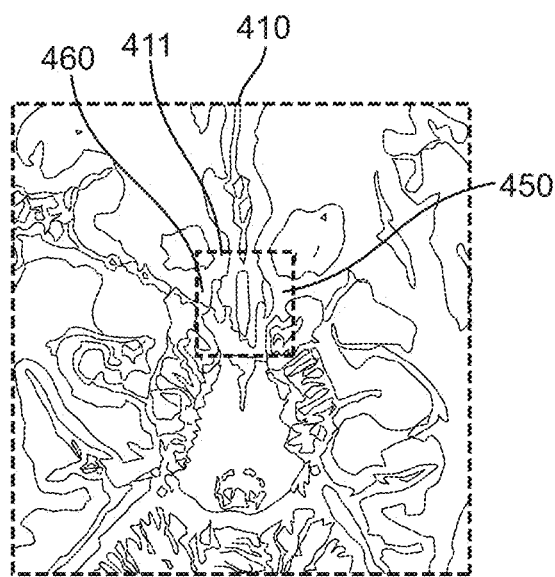
Figure 6C:
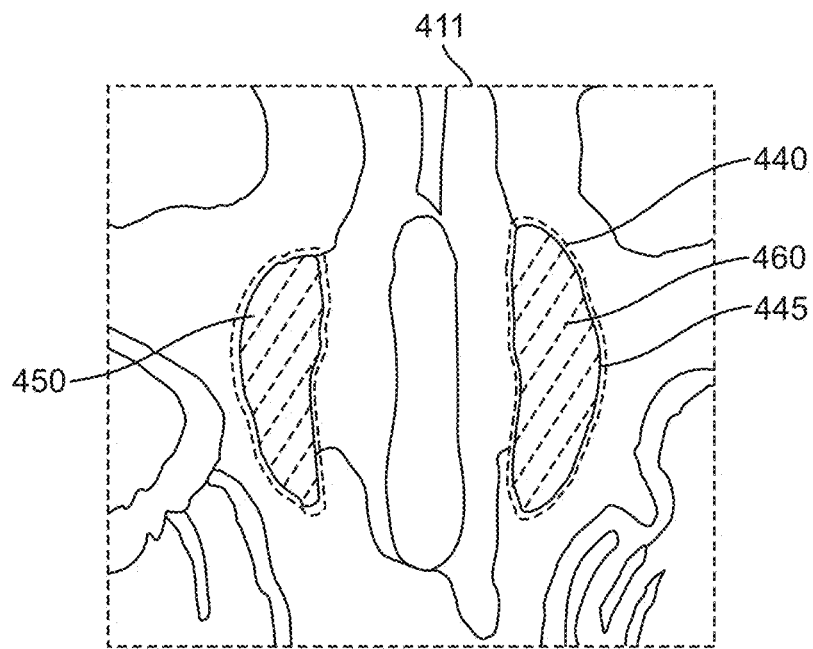

In FIG. 6A, patient 400 is treated with radiation beams 415 (representative example of other radiation beams, also illustrated as dotted lines with arrows). These radiation beams may come from any number of sources known in the art, including the Cyberknife (Accuray, Inc., Santa Clara, Calif.), or Gamma Knife 405 (Elekta, Stockholm, Sweden), or Trilogy system (Varian Medical, Palo Alto, Calif.). Additionally, ion beam particle therapy may be utilized for this and the other treatments described herein (IBA, Belgium). Beams 420 are shown aimed at right lateral hypothalamic area 415, which lies within the dashed lines bounding region 410. FIGS. 6B and 6C illustrates an intermediate 410 view and a closeup view 411 of the region, respectively. The target here includes both the right lateral hypothalamic area 450, and left lateral hypothalamic nucleus 460, both nuclei shaded in the diagrams for illustrative purposes. The desired radiomodulation effects may be achieved, for example, by delivering a marginal dose such as 65 Grey of radiation to each of those targets, with subsequent fractions delivered as needed. A steep gradient 440 adjacent the anatomical boundaries 445 of the target neural tissues limits collateral damage to adjacent tissues.

Figure 7:
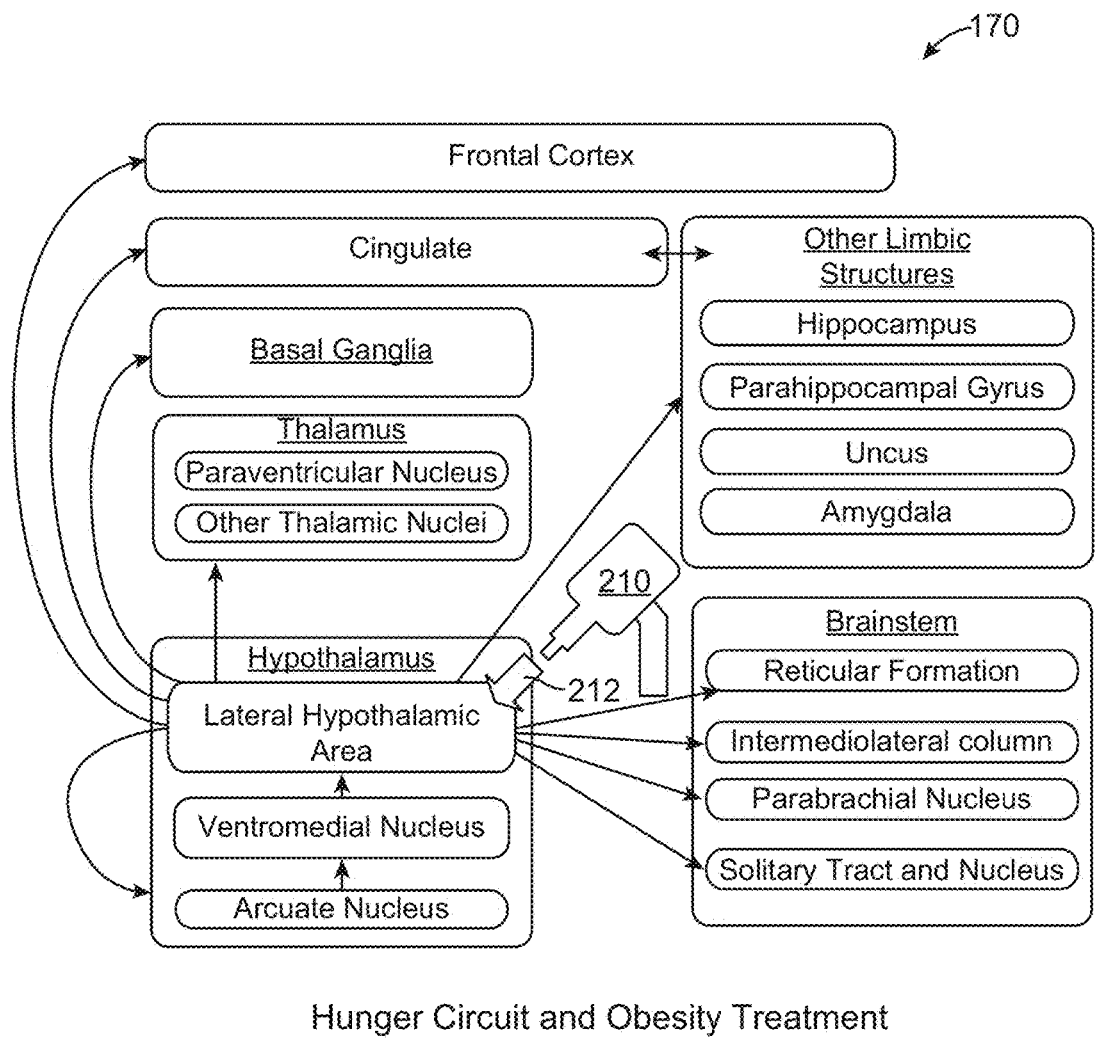
FIGS. 7, 8, and 9 schematically illustrate neural circuits associated with hyperphagia or obesity, addiction, and OCD, respectively, along candidate target tissues for treatment of each of these behavioral disorders according to embodiments of the present invention.
Figure 8:
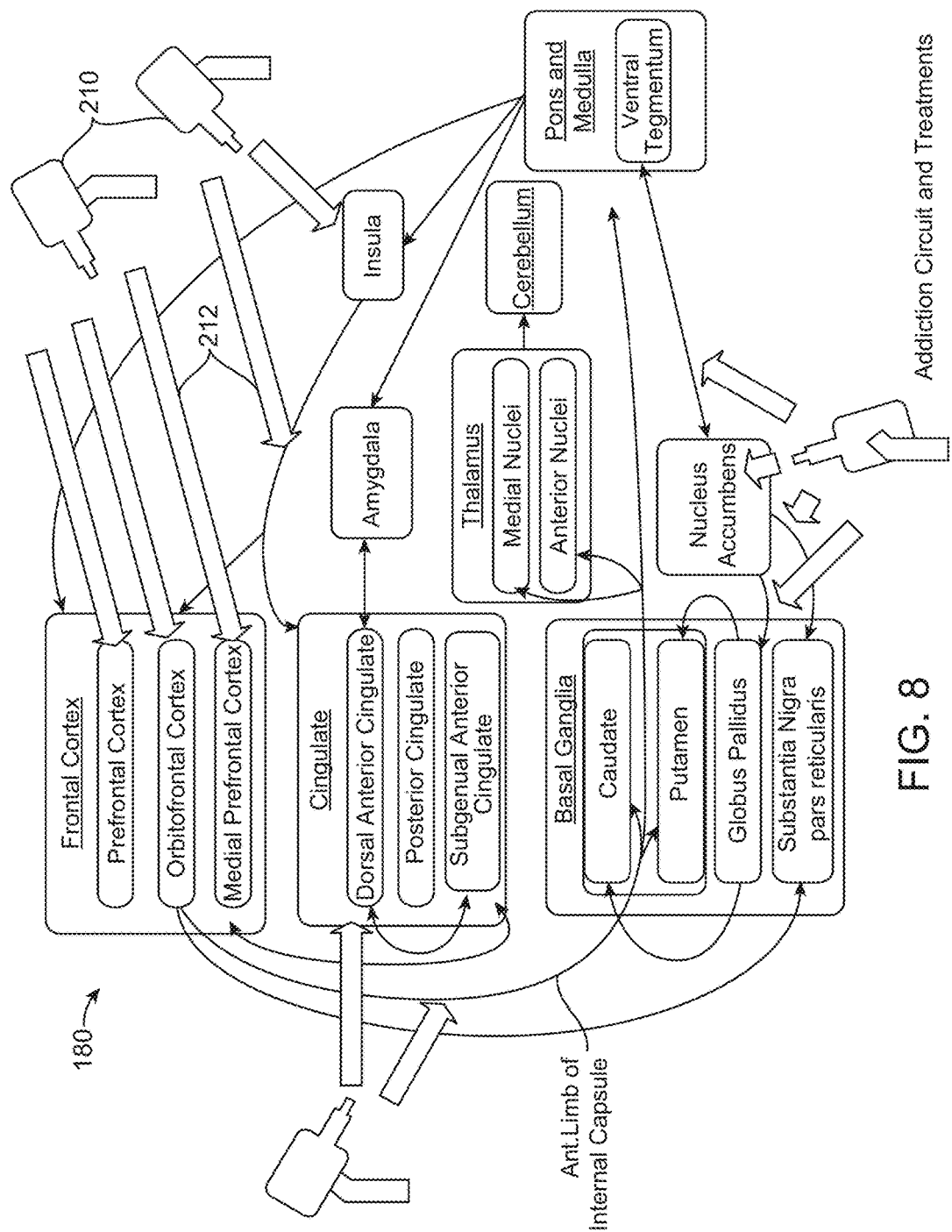
Figure 9:
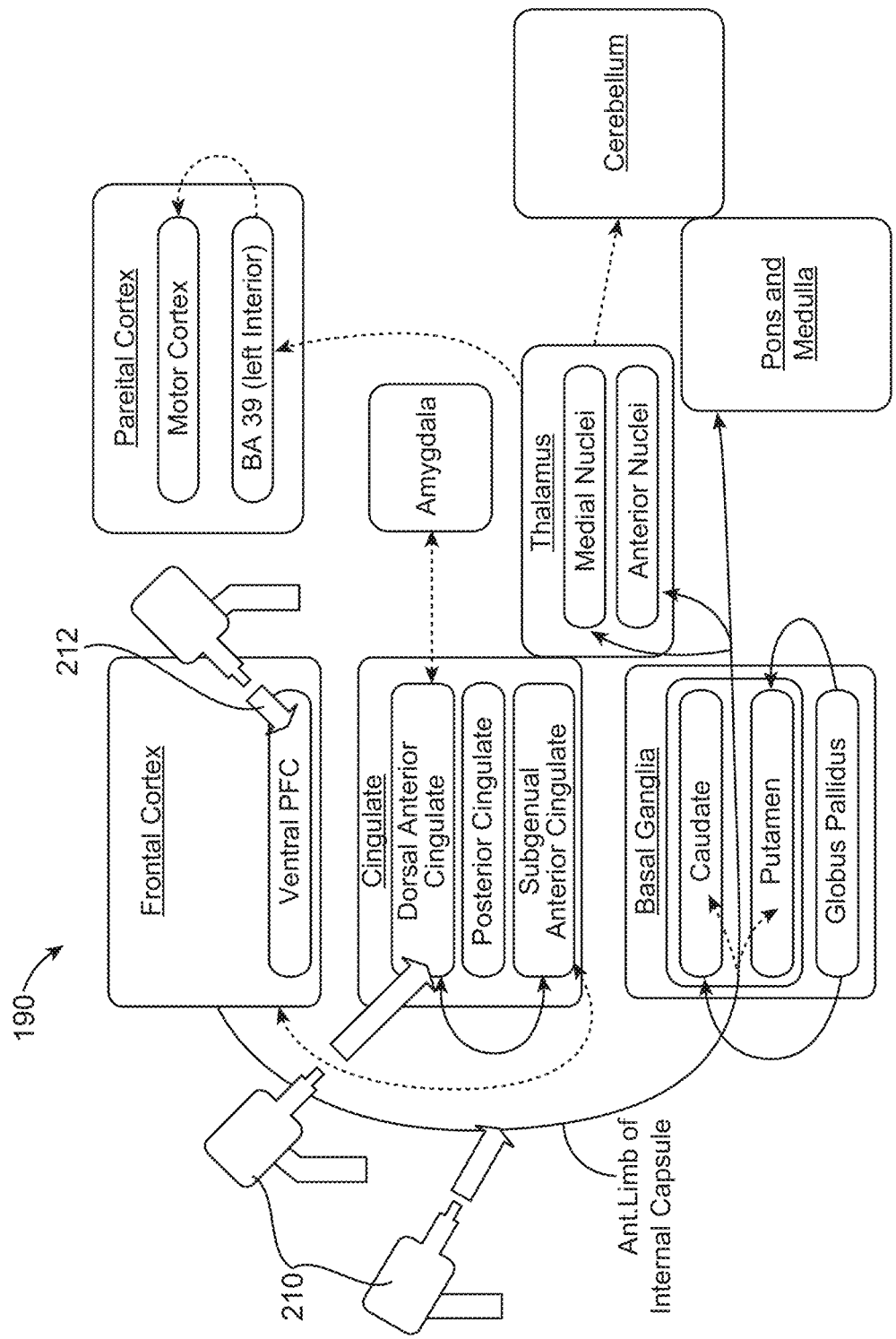

FIGS. 7-9 schematically illustrate neural circuits associated with hyperphagia or obesity, addiction, and OCD, respectively. First addressing FIG. 7, exemplary target neural tissues included in a neural circuit 170 associated with hunger and obesity are again identified using a schematic radiation source 210 and associated radiation beam 212 directed to the target tissues. The solid small arrows shown on this neural circuit diagram schematically illustrate neural connections. Candidate target tissues of neural circuit 170, as shown in FIG. 7, may include the lateral hypothalamic area, the portion of the brain which creates the sensation of hunger. Other tissues included in neural circuit 170 include the frontal cortex, cingulate, basal ganglia, the thalamaus, the paraventricular nucleus of the thalamus, other thalamic nuclei, the hypothalamus, the ventromedial nucleus of the hypothalamus, the arcuate nucleus of the hypothalamus, the brainstem, the reticular formation of the brain stem, the intermediolateral column of the brainstem, the parabrachial nucleus of the brainstem, the solitary tract and nucleus of the brainstem, and other limbic structures including the hippocampus, the parahippocampal gyms, the uncus and the amygdala.

Referring now to FIG. 8, exemplary target neural tissues included in a neural circuit 180 associated with addiction are again identified using a schematic radiation source 210 and associated radiation beam 212 directed to the target tissues. The solid small arrows shown on this neural circuit diagram schematically illustrate neural connections. Candidate target tissues of neural circuit 180, as shown in FIG. 8, may include the prefrontal cortex, orbitofrontal cortex, medial prefrontal cortex, the dorsal anterior cingulate, the insula, the neural connection between the insula and the cingulate, the anterior limb of the internal capsule, the nucleus accumbens, the neural connection between the nucleus accumbens and the ventral tegmentum, the neural connection between the nucleus accumbens and the substantia nigra pars reticularis and the neural connection between the nucleus accumbens and the globus pallidus. Other tissues included in neural circuit 180 include the posterior cingulate, the subgenual anterior cingulate, the amygdala, the thalamus, the medial nuclei of the thalamus, the anterior nuclei of the thalamus, the cerebellum, the pons, the medulla, the ventral tegmentum and the basal ganglia, including the caudate, the putamen, the globus pallidus and the substantia nigra pars reticularis.

Referring now to FIG. 9, exemplary target neural tissues included in a neural circuit 190 with Obsessive-Compulsive Disorder (OCD) are once again identified using a schematic radiation source 210 and associated radiation beam 212 directed to the target tissues. The solid small arrows shown on this neural circuit diagram schematically illustrate known neural connections. The dashed arrows shown on this neural circuit diagram schematically illustrate hypothesized connections. Candidate target tissues of neural circuit 190, as shown in FIG. 9, may include the ventral prefrontal cortex (PFC), the dorsal anterior cingulate and the anterior limb of the internal capsule (Ant. Limb of Internal Capsule). Other tissues included in neural circuit 190 include the frontal cortex, the parietal cortex, the motor cortex, Brodmann area 39, the cingulate, the posterior cingulate, the subgenual anterior cingulate, the amygdala, the basal ganglia, the caudate of the basal ganglia, the putamen of the basal ganglia, the globus pallidus of the basal ganglia, the thalamus, the medial nuclei of the thalamus, the anterior nuclei of the thalamus, the cerebellum, the pons and medulla.

Figure 10:
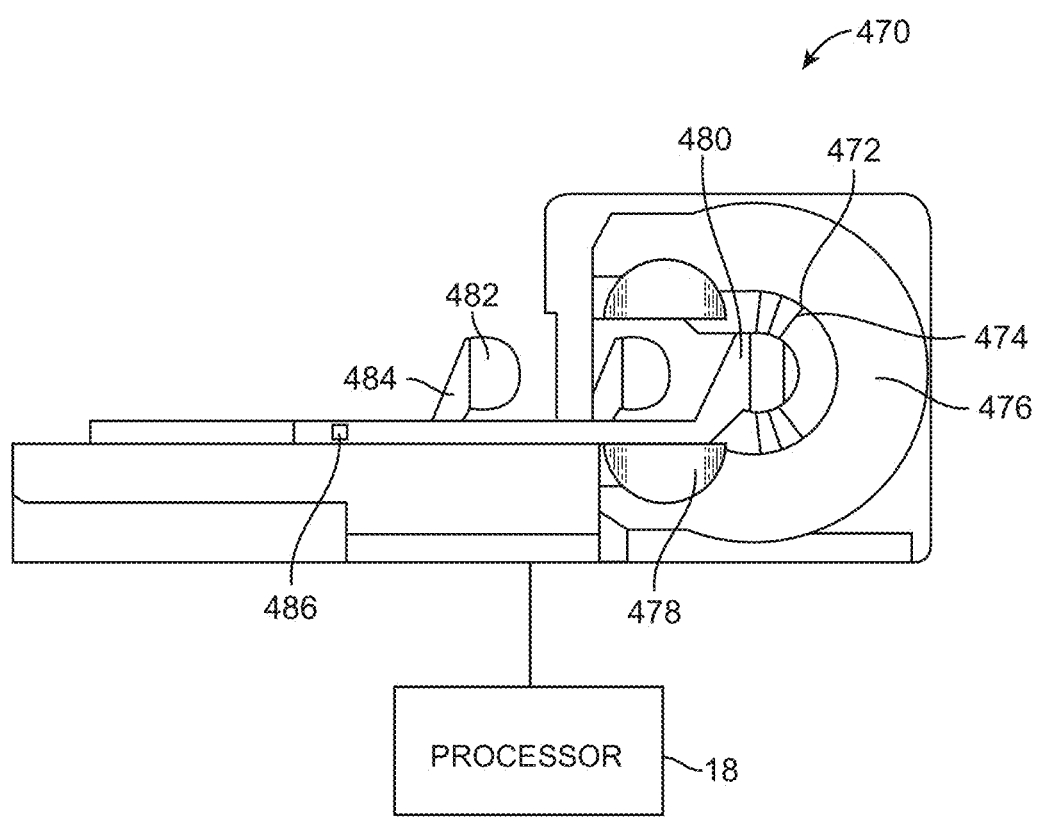
FIG. 10 schematically illustrates an alternative stereotactic radiosurgical system for implementing behavioral disorder treatments according to embodiments of the present invention.

Referring now to FIG. 10, radiosurgical systems having quite different structures may be employed in the treatments of behavioral disorders described herein. Here, a radiosurgical system 470 includes a radiation source having a spherical array of discrete cobalt 60 sources 472, with each source having an associated collimator 474 so as to direct a beam of radiation radially inwardly. Shielding 476 and doors 478 limit release of radiation, and an automated positioning system 480 helps position the target tissues at the center of the radiation beam trajectories. A helmet 482 is rigidly affixed to the head of the patient, and may include at least a portion of the collimators. The helmet is mounted to helmet supports 484, and the helmet and patient (on a movable treatment surface 486) are translated into alignment with the radiation source. Hence, at least some of the radiation beams may be delivered simultaneously, with the alignment and dosages again being determined by processing system 18.

Figure 11:
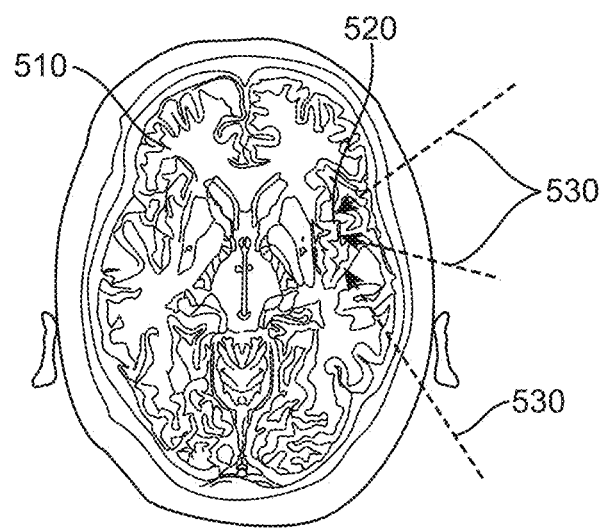
FIG. 11 schematically illustrates radiosurgical neuromodulation of the insula for treating addicition and/or other behavioral disorders.

A wide variety of behavioral disorders and conditions may be treated using the systems and method described herein. FIG. 11 illustrates a method for treatment of addiction (for example nicotine addiction) by radiomodulation (in this exemplary embodiment by irradiation of the insula). Addiction is associated with a variety of brain functions, including reward and expectation, and the driving neuroanatomic sources of addiction may vary between individuals. A patient with brain 510 has a region known as the insula. After the specific site of metabolic abnormality within the insula has been localized (for example by cued-state PET or fMRI) that locus, insula target 520 may be treated. Representative sample radiation beams 530 are shown converging upon insula target 520. For example the desired radiomodulation effects may be achieved by delivering a dose such as a marginal dose of 65 Grey of radiation to each of those targets, with subsequent fractions delivered as needed.

Alternative embodiments of radiomodulation methods for treatment of addiction may also be provided. For example, the nucleus accumbens and septum may be used to decrease drug craving in the context of addiction. In an alternative embodiment, radiomodulation of hypermetabolic activity observed at the genu of the anterior cingulate can be used to decrease drug craving. Alternatively, radiomodulation of the arcuate nucleus of the medial hypothalamus which contain peptide products of pro-opiomelanocortin (POMC) and cocaine-and-amphetamine-regulating transcript (CART) can also be used to decrease drug addiction behavior.

Figure 12:
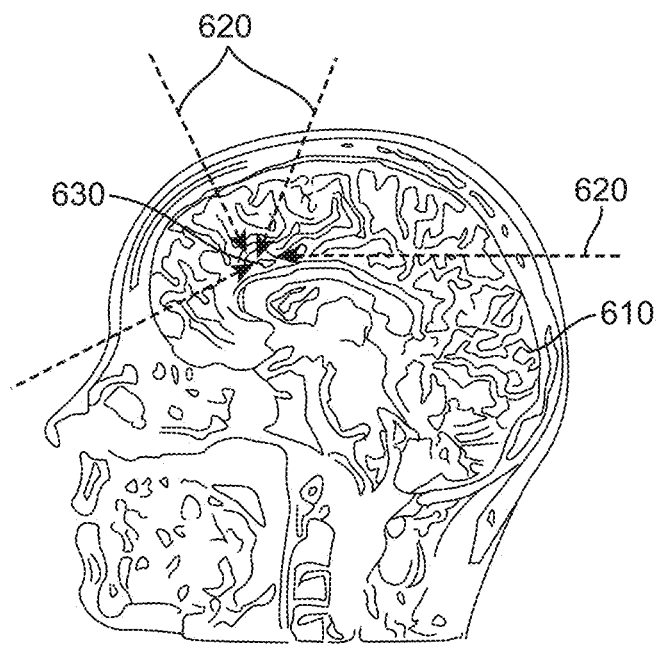
FIG. 12 schematically illustrates representative trajectories to effect radiosurgical neuromodulation of the dorsal anterior cingulate gyrus (Cg24, 32) for treating OCD, depression, and/or other behavioral disorders.

Additionally, addiction may be effectively treated by radiomodulation of the anterior cingulate cortex. This same treatment is also effective for obsessive-compulsive disorder. FIG. 12 illustrates the radiomodulation of the anterior cingulate cortex. Brain 610 includes anterior cingulate cortex target 630. Representative sample radiation beams 620 are shown converging upon anterior cingulate cortex target 630. The desired radiomodulation effects may be achieved, for example, by delivering a marginal dose such as 65 Grey of radiation to each of those targets, with subsequent fractions delivered as needed.

Obsessive-Compulsive Disorder (OCD) may also be treated by radiomodulation treatments. Destructive lesions to the anterior capsule, and analogous DBS to that region are established means of treating severe, intractable OCD. Such approaches may be emulated (with less damage to the tissue, and potentially, less damage to higher cognitive functions) using radiomodulation to the anterior limb of the internal capsule, or alternatively, to regions such as the dorsal anterior cingulate cortex,which show metabolic decrease as OCD remits). The desired radiomodulation effects may be achieved, for example, by delivering a dose such as 70 Grey of radiation to each of those targets, with subsequent fractions delivered as needed.

In some embodiments, the radiosurgical neuromodulation methods and systems described herein may be used to treat anxiety disorders, particularly through selective targeting of the amygdala's basolateral complex (abbreviated BL). The targeted BL may include the lateral, basal, and accessory basal nuclei. Sensory signals from the environment may enter the BL, including from the prefrontal cortices and the insula. Subsequently, neurons in the basolateral complex encode fear-related memories associated with these sensory signals. These brain changes may manifest in pathological states. For example, in post-traumatic stress disorder (PTSD), vivid "flashbacks" of a traumatic experience may occur. In conditions of phobia, a patient may experience dread about a certain object or situation. In panic disorder, the focus of the anxiety frequently becomes cyclical, as patients begin to fear having another episode of intense fear. In alternative embodiments, reduction of anxiety may be achieve by targeting the central medial nuclei (CeM) of the amygdala, or by targeting the central nuclei (Ce) of the amygdala, which are similarly involved in inducing fear, long after the utility of fear to promote survival has long since passed.

Figure 13:
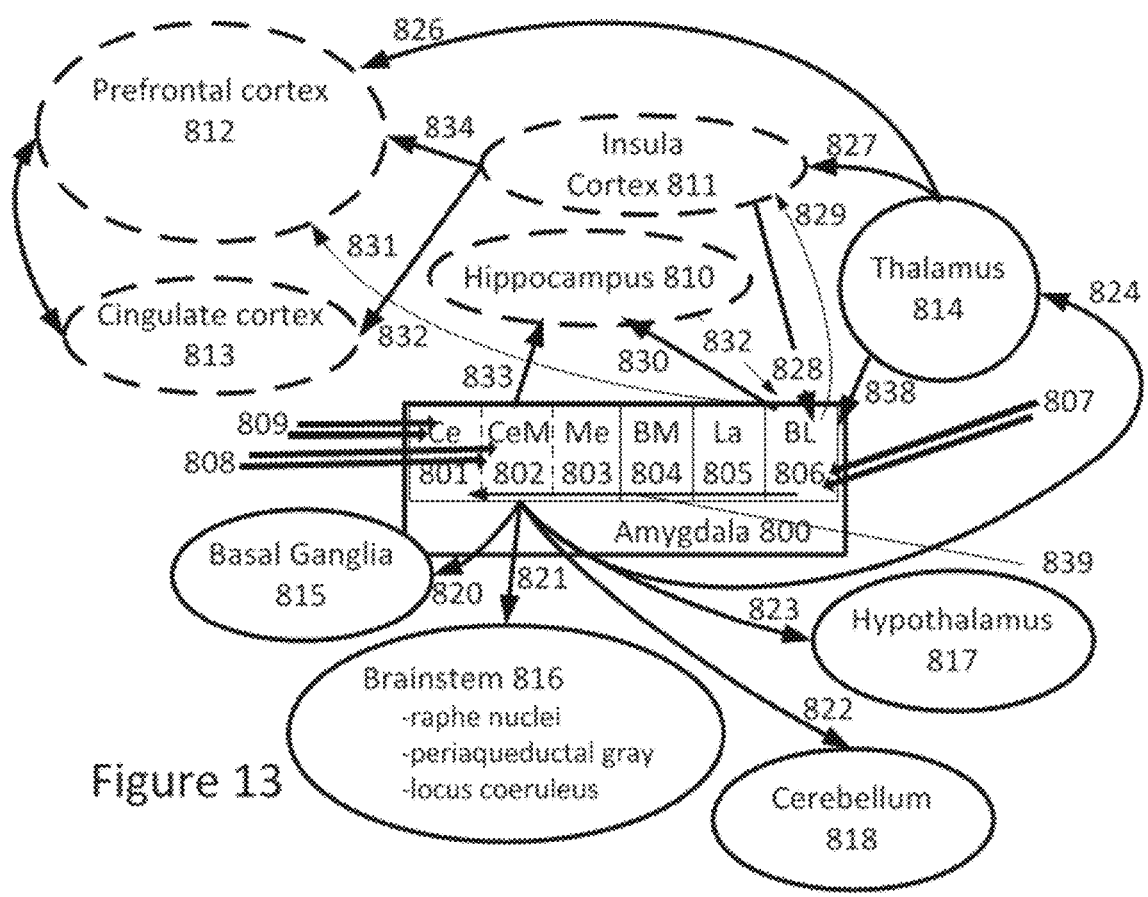
FIG. 13 illustrates a brain circuit for the production and regulation of anxiety, including the amygdala and several of the sub-region nuclei of which it is comprised. In particular the basolateral nucleus complex (BL 806) is a major center for neuronal inflow and outflow which may be targeted and treated by the method described in order to address specific symptoms of an anxiety-related behavioral disorder.

FIG. 13 illustrates a brain circuit that serves the production and regulation of anxiety. Features or elements of the circuit include the amygdala and several of the sub-region nuclei of which it is comprised. Amygdala 800 is comprised of subregions including central nucleus (Ce 801), centromedial nucleus (CeM 802), medial nucleus (Me 803), basomedial nucleus (BM 804), lateral nucleus (La 805) and basolateral complex of nuclei (BL 806). CeM 802 includes nerve tracts originating in Ce 801 and Me 803,and in some embodiments is a preferred target for the neuromodulation method herein described. BL 806 also has input connections 839 to Ce 801, which, along with Me 803 contribute fibers to the CeM 802, which in some embodiments is a preferred target for the neuromodulation method herein described. Other amygdala nuclei and subnuclei are also normally present, but not represented in these figures.

Prefrontal cortex 812 is comprised of medial and dorsolateral cortices, as well as other regions. Prefrontal cortex 812 receives input 826 from thalamus 814, input 834 from insula cortex 811, and input 831 from BL 806. Cingulate cortex 813 both receives and sends two-way information flow to and from prefrontal cortex 812, and receives input from insula cortex 811. Hippocampus 810 receives input 833 from CeM 802. Cingulate cortex 813 receives inputs from insula cortex 811 via connection 832, and has reciprocal 2-way connectivity with prefrontal cortex 812. Insula cortex 811 receives input from thalamus 814 via connection 827, and provides outputs to prefrontal cortex 812 via connection 834 and outputs to cingulate cortex 812 via connection 832. Hippocampus 810 receives input connection 830 from BL 806, and reciprocally sends output connection 832 back to BL 806. Hippocampus 810 also receives input connection 833 from CeM 802. Thalamus 814 receives input from CeM 802 via connection 824, and sends output connection 826 to prefrontal cortex 812; output connection 827 to insula cortex 811, and connection 838 to BL 806.

Hypothalamus 817 receives input from CeM 802 via connection 823. Cerebellum 818 receives input from CeM 802 via connection 822. Brainstem 816 includes subregions including the raphe nuclei and periaqueductal gray and locus ceruleus, each of which receives input from CeM 802 via connection 821. Basal Ganglia 815 receives input from CeM 802 via connection 820. In an exemplary treatment to alter activity of this circuit, stereotactic radiosurgical beam pattern 807 is targeted upon BL 806, or upon a portion of BL 806. In an alternative embodiment, stereotactic radiosurgical beam pattern 809 is targeted upon CeM 802. In another alternative embodiment, stereotactic radiosurgical beam pattern 808 is targeted upon Ce 801 or a portion of it.

Figure 14:
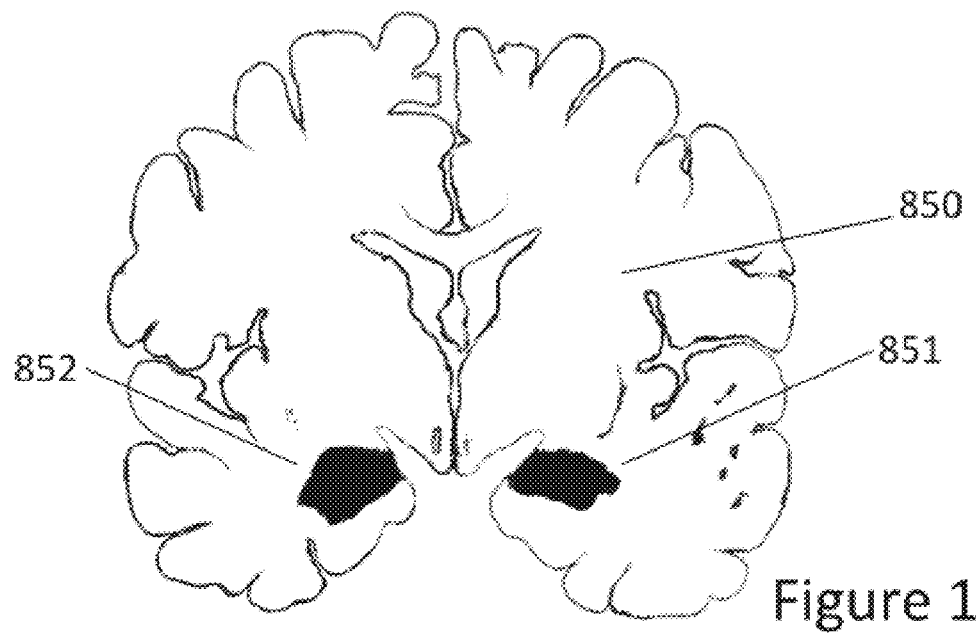
FIG. 14 illustrates the location of the right and left amygdala, respectively, within a coronal cross-section of the brain.

FIG. 14 illustrates the location of a person's right amygdala 852 and left amygdala 851, within a coronal cross-section of the brain.

Figure 15:
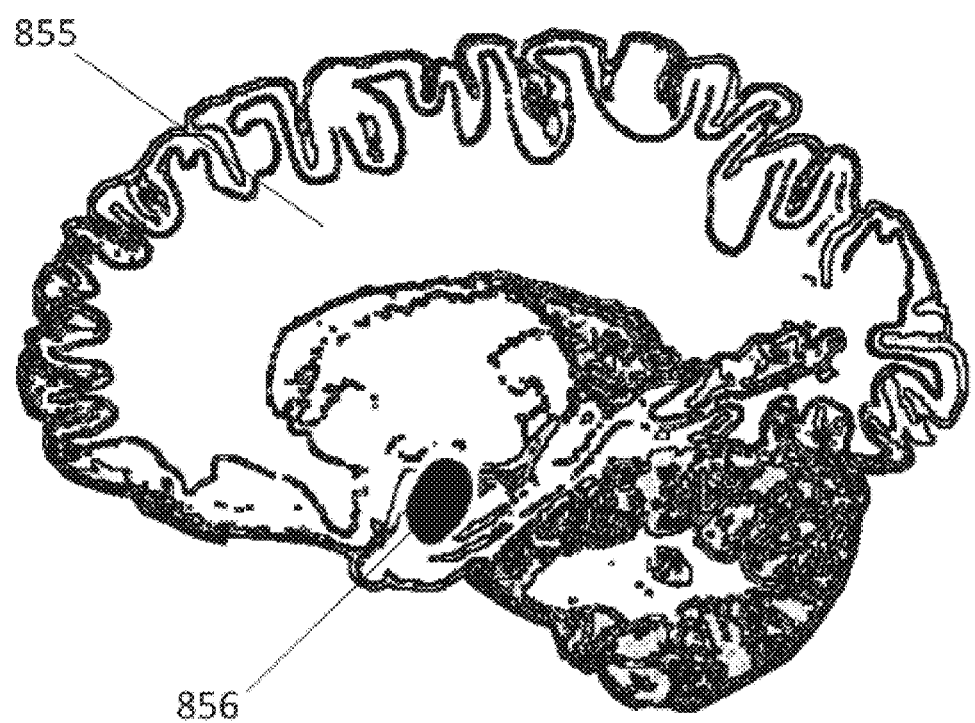
FIG. 15 illustrates the location of the amygdala within a sagittal cross-section of the brain.

FIG. 15 illustrates the location right amygdala 856 within a sagittal hemisection of the brain, within the temporal lobe. The left amygdala is not shown as it resided in the removed sagittal hemisection that is not shown.

Figure 16:
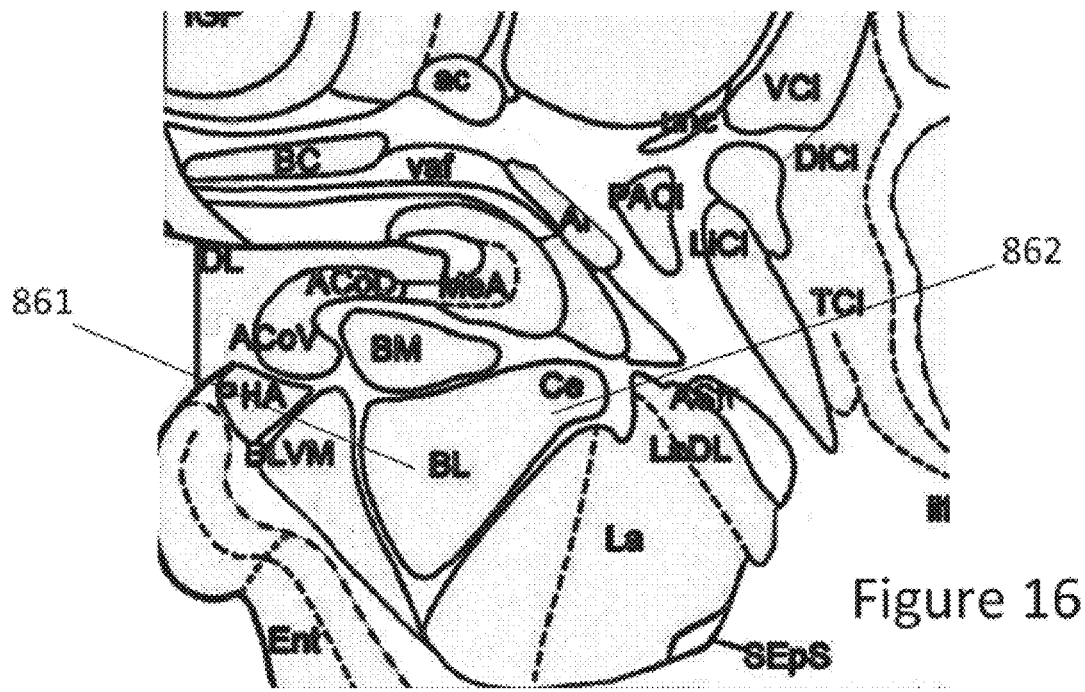
FIG. 16 illustrates the locations of the basolateral nucleus complex (BL 806), within the amygdala as shown in the Mai brain atlas.

FIG. 16 illustrates the locations of central nucleus Ce 862 (a target in some embodiments) and the basolateral complex BL 861 (a target in some embodiments) within the amygdala in a coronal section of a temporal lobe of the brain.

Figure 17:
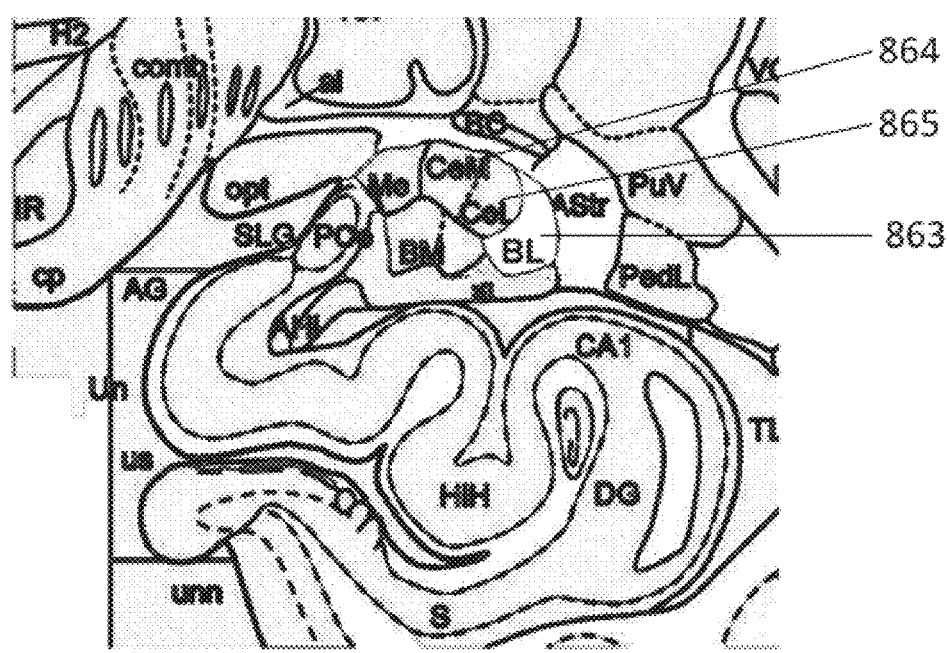
FIG. 17 provides another view of the locations of the central nucleus and the basolateral nucleus complex (BL 806) of the amygdala 800 as shown in the Mai brain atlas.

FIG. 17 illustrates the locations of centromedial complex CeM 864 (a target in some embodiments), central amygdalar complex, lateral portion CeL 865, and basolateral complex BL 861 as they appear in a more posterior coronal section of the temporal lobe. Additional details regarding the structures illustrated in FIGS. 16 and 17 can be found with reference to the Mai brain atlas.

Figure 18:
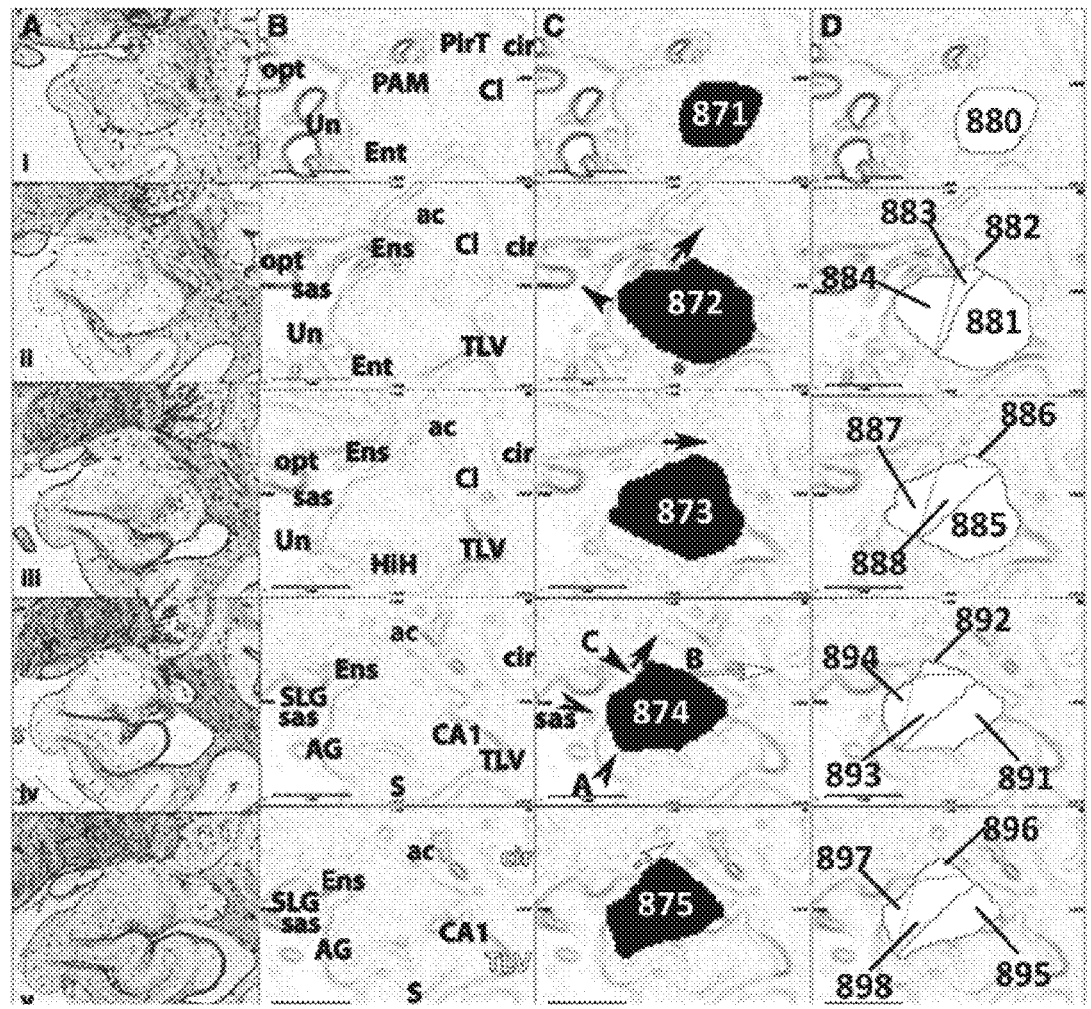
FIG. 18 illustrates an approach to segmenting MRI images of the amygdala into subregions.

FIG. 18 schematically illustrates an approach to segmenting MRI images of the amygdala into subregions, for which additional details can be found in the publications of Entis et al. In the top row, whole amygdala coronal section 871 shown in a slice that consists entirely of BL 880. In the second row, whole amygdala coronal section 872 may be segmented into BL 881, CeM 882 (a target in some embodiments), BM 883 and amygdaloid cortical complex (ACo) 884. In the third row, whole amygdala coronal section 873 may be segmented into BL 885, CeM 886, ACo 887 and BM 884. In the fourth row, whole amygdala coronal section 874 may be segmented into BL 891, CeM 886, ACo 887 and BM 888. In the fifth and last row of the figure, whole amygdala coronal section 875 may be segmented into BL 895 (a target in some embodiments), CeM 896 (a target in some embodiments), ACo 897, and BM 898. By selecting from these segmentations, for example BL 880, 881, 885, 891 and 895 and other corresponding BL sections from additional planes not illustrated here, the basolateral nucleus may be set up as a target using the radiosurgical planning software.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A method for treating a psychiatric anxiety disorder of a patient, the disorder associated with a level of localized neuronal activity within a brain of the patient as well as deleterious anxiety by the patient, the method comprising:
   identifying a portion of an amygdala on at least one side of the brain of the patient associated with the disorder; and
   inducing glial cell changes in the identified portion of the amygdala without damaging surrounding neural tissues by transmitting a cellularly sub-lethal quantity of ionizing radiation from outside the patient selectively into the identified portion of the amygdala of the brain of the patient thereby altering the level of neuronal activity such that the anxiety of the patient is mitigated.

2. The method of claim 1, wherein the portion of the amygdala is included within a basolateral complex of nuclei within the amygdala.

3. The method of claim 1, wherein the portion of the amygdala is included within a centromedial nucleus of nuclei within the amygdala.

4. The method of claim 1, wherein the portion of the amygdala is included within the central nuclei within the amygdala.

5. The method of claim 1, wherein the portion comprises a sub region included within a limited portion of discrete tissue structures of the amygdala such that at least a region of a boundary of the portion is disposed within, and separate from, anatomical boundaries of the amygdala.

6. The method of claim 1, wherein the ionizing radiation is transmitted from a radiation source as a plurality of radiation beams, and further comprising planning the radiation beams so that radiation outside the portion drops off sufficiently to inhibit collateral damage to adjacent neural tissues of the amygdala.

7. The method of claim 6, wherein the portion has a volume of less than 1000 mm3.

8. The method of claim 1, further comprising clinically determining that the disorder falls within an accepted psychiatric standard before transmitting the radiation, and verifying that the anxiety is mitigated per a clinical evaluation after transmitting the radiation.

9. The method of claim 8, further comprising identifying or verifying the portion of the amygdala by imaging differing localized neuronal activity levels within regions of the amygdala of the patient.

10. The method of claim 1, wherein the sub-lethal quantity of radiation comprises, during a single treatment, a dose in a range from about 50 Gy to about 100 Gy within the portion.

11. The method of claim 1, wherein the disorder comprises Post-Traumatic Stress Disorder (PTSD).

12. The method of claim 1, wherein said disorder comprises Generalized Anxiety Disorder (GAD).

13. The method of claim 1, wherein said disorder comprises Panic Disorder.

14. The method of claim 1, wherein said disorder comprises Social Phobia.

15. The method of claim 1, wherein the anxiety disorder comprises Specific Phobia.

16. The method of claim 1, wherein the glial cell changes in the identified portion of the amygdala comprise astrocytosis in the identified portion of the amygdala.

17. The method of claim 1, wherein the glial cell changes in the identified portion of the amygdala comprise reduction in myelin sheathing extending from oligodendrocytes in the identified portion of the amygdala.

18. The method of claim 1, wherein the glial cell changes in the identified portion of the amygdala comprise microglial increase in the identified portion of the amygdala.

* * * * *